United States Patent
Wang

(10) Patent No.: US 10,763,547 B1
(45) Date of Patent: Sep. 1, 2020

(54) ELECTROLYTE AND A BATTERY WITH SAID ELECTROLYTE

(71) Applicant: High Tech Battery Inc., Sinyi District, Taipei (TW)

(72) Inventor: Kuei Yung Wang, Taipei (TW)

(73) Assignee: High Tech Battery Inc., Taipei (TW)

(*) Notice: Subject to any disclaimer, the term of this patent is extended or adjusted under 35 U.S.C. 154(b) by 0 days.

(21) Appl. No.: 16/733,608

(22) Filed: Jan. 3, 2020

Related U.S. Application Data

(60) Provisional application No. 62/904,828, filed on Sep. 24, 2019.

(51) Int. Cl.
| | |
|---|---|
| H01M 10/056 | (2010.01) |
| H01M 10/0567 | (2010.01) |
| H01M 10/0525 | (2010.01) |
| H01M 10/42 | (2006.01) |
| H01M 10/0568 | (2010.01) |
| H01M 10/0569 | (2010.01) |
| C07D 295/037 | (2006.01) |
| H01G 9/022 | (2006.01) |

(52) U.S. Cl.
CPC .... H01M 10/0567 (2013.01); C07D 295/037 (2013.01); H01G 9/022 (2013.01); H01M 10/0525 (2013.01); H01M 10/0568 (2013.01); H01M 10/0569 (2013.01); H01M 10/4235 (2013.01); H01M 2300/0025 (2013.01)

(58) Field of Classification Search
CPC ......... H01M 10/0525; H01M 10/0567; H01M 10/0568; H01M 10/0569; H01M 10/4235; H01G 9/022; C07D 295/037

USPC ........................................................ 429/331
See application file for complete search history.

(56) References Cited

U.S. PATENT DOCUMENTS

| | | | | |
|---|---|---|---|---|
| 8,029,689 B2 * | 10/2011 | Nishida | ............... | H01G 9/038 |
| | | | | 252/62.2 |
| 8,236,446 B2 * | 8/2012 | Lu | ............... | H01M 4/133 |
| | | | | 429/209 |
| 9,406,976 B2 * | 8/2016 | Jeong | ............... | H01M 10/052 |
| 9,624,160 B2 * | 4/2017 | Schmidt | ............... | C07C 211/63 |
| 10,283,813 B1 * | 5/2019 | Wang Chen | ............... | H01M 2/162 |
| 2008/0193853 A1 * | 8/2008 | Kim | ............... | C07D 295/088 |
| | | | | 429/328 |
| 2010/0304225 A1 * | 12/2010 | Pascaly | ............... | H01G 11/62 |
| | | | | 429/342 |
| 2012/0318360 A1 * | 12/2012 | Kawata | ............... | C07D 233/58 |
| | | | | 136/263 |
| 2014/0134501 A1 * | 5/2014 | Li | ............... | H01M 10/052 |
| | | | | 429/339 |
| 2015/0280283 A1 * | 10/2015 | Oyama | ............... | H01M 10/052 |
| | | | | 429/188 |

(Continued)

FOREIGN PATENT DOCUMENTS

WO   WO-2019081907 A1 *   5/2019   ............ C07F 9/5414

*Primary Examiner* — Amanda C. Walke
(74) *Attorney, Agent, or Firm* — Leydig, Voit & Mayer, Ltd.

(57) ABSTRACT

An electrolyte for a lithium-ion battery, and a battery incorporating the electrolyte. The electrolyte includes a lithium salt, a non-aqueous organic solvent which includes a carbonate-based solvent, a flame retardant, a film former, and a stabilizing medium. The flame retardant includes $PYR_{1R}PF_6$ (N-Methyl-N-alkylpyrrolidinium Hexafluorophosphate Salt).

27 Claims, 22 Drawing Sheets

| No. | Product | Material 1 | alkyl halide | Reaction temperature | Reaction time |
|---|---|---|---|---|---|
| 1 | $PYR_{12}Br$ | NMPD | 1-ethyl bromide | 5°C | 2hr |
| 2 | $PYR_{13}Br$ | NMPD | 1-propyl bromide | 10°C | 2hr |
| 3 | $PYR_{14}Br$ | NMPD | 1-butyl bromide | 10°C | 2hr |
| 4 | $PYR_{15}Br$ | NMPD | 1-pentyl bromide | 60°C | 2hr |
| 5 | $PYR_{16}Br$ | NMPD | 1-hexyl bromide | 60°C | 2hr |
| 6 | $PYR_{17}Br$ | NMPD | 1-heptyl bromide | 70°C | 2hr |
| 7 | $PYR_{18}Br$ | NMPD | 1-octyl bromide | 70°C | 2hr |
| 8 | $PYR_{19}Br$ | NMPD | 1-Nonyl bromide | 70°C | 2hr |
| 9 | $PYR_{110}Br$ | NMPD | 1-Decyl bromide | 70°C | 2hr |

Note: 1. NMPD : N methyl pyrrolidine
2. molar ratio : NMPD : alkyl halide = 1:1.1
3. alkyl halide:DI water = 1:1 vol%

(56) References Cited

U.S. PATENT DOCUMENTS

| | | | |
|---|---|---|---|
| 2016/0254545 A1* | 9/2016 | Sugita | H01M 4/62 429/233 |
| 2017/0162906 A1* | 6/2017 | Nakazawa | H01M 10/0569 |
| 2019/0140309 A1* | 5/2019 | Lamanna | H01M 10/0525 |

* cited by examiner

| No. | Product | Material 1 | alkyl halide | Reaction temperature | Reaction time |
|---|---|---|---|---|---|
| 1 | PYR$_{12}$Br | NMPD | 1-ethyl bromide | 5°C | 2hr |
| 2 | PYR$_{13}$Br | NMPD | 1-propyl bromide | 10°C | 2hr |
| 3 | PYR$_{14}$Br | NMPD | 1-butyl bromide | 10°C | 2hr |
| 4 | PYR$_{15}$Br | NMPD | 1-pentyl bromide | 60°C | 2hr |
| 5 | PYR$_{16}$Br | NMPD | 1-hexyl bromide | 60°C | 2hr |
| 6 | PYR$_{17}$Br | NMPD | 1-heptyl bromide | 70°C | 2hr |
| 7 | PYR$_{18}$Br | NMPD | 1-octyl bromide | 70°C | 2hr |
| 8 | PYR$_{19}$Br | NMPD | 1-Nonyl bromide | 70°C | 2hr |
| 9 | PYR$_{110}$Br | NMPD | 1-Decyl bromide | 70°C | 2hr |

Note:
1. NMPD : N methyl pyrrolidine
2. molar ratio : NMPD : alkyl halide = 1:1.1
3. alkyl halide:DI water = 1:1 vol%

Figure 1

| Item | side reaction | oganic electrolyte(OE) + ionic liquid (IL) | | | |
|---|---|---|---|---|---|
| | | 5w t% | 10w t% | 15w t% | 20w t% |
| PYR$_{12}$PF$_6$ | YES | cycle life no more than 100 times at capacity remain 80% | | | |
| PYR$_{13}$PF$_6$ | YES | | | | |
| PYR$_{14}$PF$_6$ | YES | | | | |
| PYR$_{15}$PF$_6$ | YES | | | | |
| PYR$_{16}$PF$_6$ | YES | | | | |
| PYR$_{17}$PF$_6$ | YES | | | | |
| PYR$_{18}$PF$_6$ | YES | | | | |
| PYR$_{19}$PF$_6$ | YES | | | | |
| PYR$_{110}$PF$_6$ | YES | | | | |
| Note | oganic electrolyte (OE): 1M LiPF$_6$ with ((EC/DMC/DEC (1:1:1 vol%)+3.5w t% VC)) | | | | |

Figure 3 electrolyte: 1 M $LiPF_6$ with ((EC/DMC/DEC (1:1:1 vol%)+3.5wt%VC+IL) + 10 wt.% $PYR_{16}PF_6$)

| No. | Item | cycle life of Negative A | cycle life of Negative B |
|---|---|---|---|
| A | oganic electrolyte (OE) | 2163 | 513 |
|  | Add ratio |  |  |
| 1 | $PYR_{12}PF_6$ 5wt% | 98 | 105 |
| 2 | $PYR_{15}PF_6$ 5wt% | 94 | 104 |
| 3 | $PYR_{16}PF_6$ 5wt% | 97 | 102 |
| 4 | $PYR_{12}PF_6$ 10wt% | 63 | 78 |
| 5 | $PYR_{15}PF_6$ 10wt% | 50 | 69 |
| 6 | $PYR_{16}PF_6$ 10wt% | 56 | 72 |
| 7 | $PYR_{12}PF_6$ 20wt% | 38 | 37 |
| 8 | $PYR_{15}PF_6$ 20wt% | 40 | 40 |
| 9 | $PYR_{16}PF_6$ 20wt% | 32 | 32 |
| 10 | $PYR_{12}PF_6 : PYR_{15}PF_6 : PYR_{16}PF_6 : OE = 10:5:5:80$ | 36 | 36 |
| 11 | $PYR_{12}PF_6 : PYR_{15}PF_6 : PYR_{16}PF_6 : OE = 5:10:5:80$ | 34 | 34 |
| Note: | remain capacity lower 80% at 0.2 C charge/discharge oganic electrolyte: 1M $LiPF_6$ with (EC/DMC/DEC (1:1:1 vol%)+3.5wt% VC) |  |  |

Figure 7

| No. | OE | PYR$_{12}$PF$_6$ | PYR$_{15}$PF$_6$ | PYR$_{16}$PF$_6$ | PYR$_{14}$BOB | PYR$_{14}$ODFB | PYR$_{14}$BMB | cycle life of Negative A | cycle life of Negative B |
|---|---|---|---|---|---|---|---|---|---|
| 1 | | 15% | | | 5% | | | 572 | 178 |
| 2 | | 15% | | | | 5% | | 558 | 182 |
| 3 | | 15% | | | | | 5% | 542 | 175 |
| 4 | | | 15% | | 5% | | | 546 | 163 |
| 5 | 80% | | 15% | | | 5% | | 537 | 149 |
| 6 | | | 15% | | | | 5% | 523 | 152 |
| 7 | | | | 15% | 5% | | | 539 | 184 |
| 8 | | | | 15% | | 5% | | 542 | 172 |
| 9 | | | | 15% | | | 5% | 512 | 167 |
| 10 | | | 10% | | 3% | | | 785 | 198 |
| 11 | 87% | | 10% | | | 3% | | 769 | 221 |
| 12 | | | 10% | | | | 3% | 743 | 203 |
| 13 | | 5% | | | 1% | | | 925 | 234 |
| 14 | 94% | 5% | | | | 1% | | 937 | 252 |
| 15 | | 5% | | | | | 1% | 909 | 226 |
| 16 | 100% | | | | | | | 2163 | 513 |

Note: remain capacity lower 80% at 0.2C charge/discharge
organic electrolyte:
1M LiPF$_6$ with (EC/DMC/DEC (1:1:1 vol%)+3.5w t% VC)

Figure 8

| No. | OE | PYR$_{15}$PF$_6$ | PYR$_{14}$BOB | PYR$_{14}$ODFB | PYR$_{14}$TFSI | PYR$_{14}$FSI | cycle life of Negative A | cycle life of Negative B |
|---|---|---|---|---|---|---|---|---|
| 1 | 79% | 15% | 5% |  | 1% |  | 789 | 210 |
| 2 | 79% | 15% |  | 5% | 1% |  | 801 | 201 |
| 3 | 79% | 15% | 5% |  |  | 1% | 537 | 215 |
| 4 | 79% | 15% |  | 5% |  | 1% | 521 | 228 |
| 5 | 84% | 10% | 5% |  | 1% |  | 1321 | 241 |
| 6 | 84% | 10% |  | 5% | 1% |  | 1318 | 238 |
| 7 | 84% | 10% | 5% |  |  | 1% | 759 | 253 |
| 8 | 84% | 10% |  | 5% |  | 1% | 773 | 257 |
| 9 | 82% | 10% | 5% |  | 3% |  | 1433 | 253 |
| 10 | 82% | 10% |  | 5% | 3% |  | 1437 | 240 |
| 11 | 82% | 10% | 5% |  |  | 3% | 785 | 262 |
| 12 | 82% | 10% |  | 5% |  | 3% | 792 | 279 |
| 13 | 93% | 5% | 1% |  | 1% |  | 1345 | 299 |
| 14 | 93% | 5% |  | 1% | 1% |  | 1372 | 305 |
| 15 | 93% | 5% | 1% |  |  | 1% | 910 | 310 |
| 16 | 93% | 5% |  | 1% |  | 1% | 920 | 326 |
| 17 | 91% | 5% | 1% |  | 3% |  | 1537 | 306 |
| 18 | 91% | 5% |  | 1% | 3% |  | 1587 | 328 |
| 19 | 91% | 5% | 1% |  |  | 3% | 915 | 354 |
| 20 | 91% | 5% |  | 1% |  | 3% | 908 | 369 |
| 21 | 100% |  |  |  |  |  | 2163 | 513 |

Note: remain capacity lower 80% at 0.2C charge/discharge
organic electrolyte(OE):
Electrode A : 1M LiPF$_6$ with (EC/DMC/DEC (1:1:1 vol%)+3.5wt% VC)
Electrode B : 1M LiPF$_6$ with (EC/DMC/DEC (1:1:1 vol%)+3.5wt% FEC)

Figure 9

| No. | Main solvent | PFPN | EHDP | HPCP | DOPO-HQ | cycle life of Negative A | Self-extinguish time sec/g |
|---|---|---|---|---|---|---|---|
| 1 | (OE+IL) | 0.50% | | | | 1674 | <6 |
| 2 | | 2% | | | | 2291 | <6 |
| 3 | | 2.50% | | | | 2308 | <6 |
| 4 | | 2.90% | | | | 2315 | <6 |
| 5 | | 3% | | | | 2330 | <6 |
| 6 | | 5% | | | | 2392 | <6 |
| 7 | | 10% | | | | 2432 | <6 |
| 8 | | | 0.50% | | | 1637 | <6 |
| 9 | | | 2% | | | 1943 | <6 |
| 10 | | | 3.50% | | | 2098 | <6 |
| 11 | | | 4.50% | | | 2158 | <6 |
| 12 | | | 5% | | | 2153 | <6 |
| 13 | | | | 0.5% | | 1484 | <6 |
| 14 | | | | 2% | | 1599 | <6 |
| 15 | | | | 3.5% | | 1932 | <6 |
| 16 | | | | 4.5% | | 1908 | <6 |
| 17 | | | | 5% | | 1956 | <6 |
| 18 | | | | | 0.5% | 1957 | <6 |
| 19 | | | | | 1.5% | 2084 | <6 |
| 20 | OE | | | | | 2163 | 35 |
| 21 | OE+IL | | | | | 1396 | <6 |

Note: organic electrolyte (OE):
1M LiPF$_6$ with (EC/DMC/DEC (1:1:1 vol%))+3.5wt% VC
ionic liquid (IL):
IL = PYR$_{16}$PF$_6$ + PYR$_{14}$BOB + PYR$_{14}$TFSI = 10:1:4 wt%

PFPN — ethoxy(pentafluoro)cyclotriphosphazene
EHDP — Ethylhexyl Diphenyl Phosphate
HPCP — Hexaphenoxycyclotriphosphazene
DOPO-HQ — 10 (2,5-Dihydroxypheny)-10h-9-oxa-10-phospha-phenanthrene-10-oxide

Figure 10

| No. | oganic electrolyte | ionic liquid flame retardant | 1st stabilizer | 2nd stabilizer | side reaction |
|---|---|---|---|---|---|
| 1 | OE | - | - | - | no |
| 2 | OE | 10 w% $PYR_{16}PF_6$ | 5 w% $PYR_{14}BF_4$ | - | Yes |
| 3 | OE | 15 w% $PYR_{16}PF_6$ | 5 w% $PYR_{14}ODFB$ | - | no |
| 4 | OE | 15 w% $PYR_{16}PF_6$ | 5 w% $PYR_{14}BOB$ | - | no |
| 5 | OE | 10 w% $PYR_{16}PF_6$ | - | 5 w% $PYR_{14}FSI$ | Yes |
| 6 | OE | 10 w% $PYR_{16}PF_6$ | - | 5 w% $PYR_{14}TFSI$ | Yes |
| 7 | OE | 14 w% $PYR_{16}PF_6$ | 1w% $PYR_{14}BOB$ | 5 w% $PYR_{14}TFSI$ | no |
| 8 | OE | 9 w% $PYR_{16}PF_6$ | 1w% $PYR_{14}BOB$ | 10 w% $PYR_{14}TFSI$ | no |

Figure 11

Organic electrolyte: 1 M LiPF$_6$ with (EC/DMC/DEC (1:1:1 vol%)+3.5wt%VC)

| No. | Main solvent | PFPN | EHDP | HPCP | DOPO-HQ | cycle life of electrode A | Self-extinguish time sec/g |
|---|---|---|---|---|---|---|---|
| 1 | (OE+IL) | 2.0% | | | | 2013 | <12 |
| 2 | | 2.5% | | | | 2089 | <8 |
| 3 | | 2.9% | | | | 2149 | <8 |
| 4 | | 3% | | | | 2315 | <6 |
| 5 | | 4% | | | | 2317 | <6 |
| 6 | | 5% | | | | 2340 | <6 |
| 7 | | 10% | | | | 2452 | <6 |
| 8 | | | 4.5% | | | 2173 | <7 |
| 9 | | | 5% | | | 2188 | <6 |
| 10 | | | | 4.5% | | 2098 | <6 |
| 11 | | | | 5% | | 2134 | <6 |
| 12 | | | | | 1.5% | 2102 | <10 |
| 13 | OE | | | | | 2163 | 35 |
| 14 | OE+IL | | | | | 1873 | <25 |

Note oganic electrolyte:
1M LiPF$_6$ with (EC/DMC/DEC (1:1:1 vol%)+3.5wt% VC
ionic liquid (IL):
IL = PYR$_{16}$PF$_6$ + PYR$_{14}$BOB +PYR$_{14}$TFSI = 1:0.5:1 wt%
OE:IL=97.5:2.5 wt%

PFPN — ethoxy(pentafluoro)cyclotriphosphazene
EHDP — EthylhexylDiphenylPhosphate
HPCP — Hexaphenoxycyclotriphosphazene
DOPO-HQ — 10 (2,5-Dihydroxypheny)-10h-9-oxa-10-phospha-phenanthrene-10-oxide

Figure 20

| No. | Main solvent | PFPN | EHDP | HPCP | DOPO-HQ | cycle life of electrode A | Self-extinguish time sec/g |
|---|---|---|---|---|---|---|---|
| 1 | OE+IL | 2.5% | | | | 2078 | <8 |
| 2 | | 2.9% | | | | 2102 | <8 |
| 3 | | 3% | | | | 2311 | <6 |
| 4 | | 4% | | | | 2315 | <6 |
| 5 | | 5% | | | | 2338 | <6 |
| 6 | | 10% | | | | 2433 | <6 |
| 7 | | | 4.5% | | | 2149 | <7 |
| 8 | | | 5% | | | 2176 | <6 |
| 9 | | | | 4.5% | | 2055 | <6 |
| 10 | | | | 5% | | 2122 | <6 |
| 11 | | | | | 1.5% | 2095 | <10 |
| 12 | OE | | | | | 2163 | 35 |
| 13 | OE+IL | | | | | 1824 | <25 |
| Note | organic electrolyte: 1M LiPF6 with (EC/DMC/DEC (1:1:1 vol%)+3.5wt% VC ionic liquid (IL): IL = PYR16PF6 + PYR14ODFB +PYR13TFSI = 1:0.5:1 wt% | | | | | | |
| | PFPN | ethoxy(pentafluoro)cyclotriphosphazene | | | | | |
| | EHDP | EthylhexylDiphenylPhosphate | | | | | |
| | HPCP | Hexaphenoxycyclotriphosphazene | | | | | |
| | DOPO-HQ | 10-(2,5-Dihydroxypheny)-10h-9-oxa-10-phospha-phenanthrene-10-oxide | | | | | |

Figure 21

| No. | Main solvent | PFPN | EHDP | HPCP | DOPO-HQ | cycle life of Negative A | Self-extinguish time sec/g |
|---|---|---|---|---|---|---|---|
| 1 | OE+IL | 2.5% | | | | 2251 | <6 |
| 2 | | 2.9% | | | | 2294 | <6 |
| 3 | | 3% | | | | 2315 | <6 |
| 4 | | 5% | | | | 2337 | <6 |
| 5 | | 10% | | | | 2356 | <6 |
| 6 | | | 3.5% | | | 2043 | <6 |
| 7 | | | 4.5% | | | 2098 | <6 |
| 8 | | | 5% | | | 2156 | <6 |
| 9 | | | | 3.5% | | 1894 | <6 |
| 10 | | | | 4.5% | | 1902 | <6 |
| 11 | | | | 5% | | 1941 | <6 |
| 12 | | | | | 1.5% | 2096 | <6 |
| 13 | OE | | | | | 2163 | 35 |
| 14 | OE+IL | | | | | 1361 | <6 |

Note: organic electrolyte (OE):
1M LiPF$_6$ with (EC/DMC/DEC (1:1:1 vol%)+3.5wt% VC
ionic liquid (IL):
IL = PYR$_{16}$PF$_6$ + PYR$_{14}$ODFB + PYR$_{13}$TFSI = 10:1:4 wt%

PFPN: ethoxy(pentafluoro)cyclotriphosphazene
EHDP: EthylhexylDiphenylPhosphate
HPCP: Hexaphenoxycyclotriphosphazene
DOPO-HQ: 10 (2,5-Dihydroxypheny)-10h-9-oxa-10-phospha-phenanthrene-10-oxide

Figure 22

ELECTROLYTE AND A BATTERY WITH SAID ELECTROLYTE

The present invention relates to an electrolyte for a rechargeable battery, for example particularly, but not exclusively, for a lithium-ion battery.

BACKGROUND OF THE INVENTION

Lithium-ion battery has extensive application in diverse fields of technology. It is progressively more challenging to enhance the performance of the battery, which involves fine balancing amongst various aspects. Side reactions creep in when new combination is used, for example, sudden redox reaction at specific yet broad range of potential applied. In addition to the costs for manufacture, two main concerns are the life cycle and the stability of the battery. It is obvious that safety is the first and foremost.

Recurrently, flammability and explosion of lithium-ion batteries make the headlines of newspapers and cause concerns. The problem is usually attributable to a poor combination of electrode and electrolyte.

A solution to enhance stability would be to use Lithium Iron Phosphate (LFP) as a material for the positive electrode. Cost and pollution concerns are minimal. The special olivine structure of LFP contributes significantly to the low flammability and explosion risk due to improper handling of the battery such as overcharging, over discharging and/or short circuit.

It is common to use nonaqueous organic solvent in the electrolyte of a lithium ion battery. A mixture of two or more carbonate-based electrolytes are prevalent. The commonly used organic solvents include ethylene carbonate (EC), ethyl methyl carbonate (EMC), diethyl carbonate (DEC), propylene carbonate (PC), or dimethyl carbonate (DMC). The addition of film former agents is also customary. The common film former agents include vinyl carbonate (VC) and fluoroethylene carbonate (FEC).

All of these organic solvents and film former agents have relatively high volatility and flammability. They are more likely to contribute to an explosion in case of improper handling of a battery.

The use of ionic liquids in the electrolyte of lithium ion battery is being extensively explored because of its low volatility and low-combustion properties. It remains as molten salt that exhibits liquid state below 100 degree Celsius and around room temperature. As such they are called room temperature ionic liquids (RTIL) or room temperature molten salts.

1-alkyl-3-methylimidazolium is the most researched. Taking 1-alkyl-3-methylimidazolium tetrafluoroborate as an example, in which the alkyl chain has a carbon number of 1 to 18. In general, the melting point should increase substantially as the number of carbon chains increases. However, this may not always be the case. The melting point of an ionic liquid with 1-alkyl-3-methylimidazolium cation is substantially affected by the anion. There are many uncertainties.

In summary, the melting point of the ionic liquid depends on multiple factors including the number of carbon in the cation and the anion. For example 1-ethyl-3-methylimidazolium Cl has a melting point of 87° C., 1-ethyl-3-methylimidazolium $PF_6$ has a melting point of 62° C., 1-ethyl-3-methylimidazolium $BF_4$ has a melting point of 15 degrees.

1-ethyl-3-methylimidazolium $AlCl_4$ has a melting point of 7 degrees, and 1-ethyl-3-methylimidazolium TFSI melting point −3 degrees, Another problem would be the size of the molecular group of the ionic liquid. There is a general trend that the larger the molecular group, the higher the viscosity and the lower the conductivity. The addition of carbonate electrolytes to overcome the inherent problem with the ionic liquid brings back the aforementioned concerns on volatility, combustion and possible explosion.

The invention seeks to inhibit or at least to mitigate such shortcomings by providing a stable electrolyte useful in battery for multiple fields.

SUMMARY OF THE INVENTION

According to the invention, there is provided an electrolyte for a lithium-ion battery comprising a lithium salt, a non-aqueous organic solvent which includes a carbonate-based solvent, a flame retardant, a film former and a stabilizing medium, wherein the flame retardant comprises $PYR_{1R}PF_6$ (N-Methyl-N-alkylpyrrolidinium Hexafluorophosphate Salt) at the amount of 1 to 15 wt. % of the electrolyte. Preferably, R in $PYR_{1R}PF_6$ indicates the number of carbon atoms in the alkyl side chains, in which R is selected from any one of 2 to 10. More preferably, the $PYR_{1R}PF_6$ has a melting point greater than 200° C. It is preferable that the R is 2, 5 or 6. Preferably, the stabilizing medium includes first and second stabilizer. The first stabilizer may comprise an ionic liquid with $PYR_{1R}^+$ cation and a boron-based anion other than $BF_4^-$. Preferably, R is 2, 3, 4, 5 or 6. It is preferable that the boron-based anion is selected from a group consisting of bis(xoalateborate) (BOB), difluoro(oxalate)borate ($ODFB^-$) and bis(mandelato)borate(BMB). Advantageously, the second stabilizer comprises an ionic liquid with $PYR_{1R}^+$ cation. More advantageously, R is 3 or 4. Preferably, the second stabilizer comprises an ionic liquid with an anion selected from a group consisting of $TFSI^-$ and $FSI^-$. More preferably, the amount of the first stabilizer is between 0 to 5 wt. % of the electrolyte. It is preferable that the amount of the second stabilizer is between 0 to 10 wt. % of the electrolyte. More preferably, it comprises a third stabilizer. The third stabilizer can be selected from a group consisting of Ethoxy(pentafluoro) cyclotriphosphazene (PFPN), Ethylhexyl Diphenyl Phosphate (EHDP), Hexaphenoxycyclotriphosphazene (HPCP) and 10-(2,5-dihydroxyphenyl)-9,10-dihydro-9-oxa-10-phosphaphenanthrene-10-oxide (DOPO-HQ). Preferably, the amount of PFPN is between 0.5 to 10 wt. % of the electrolyte. More preferably, the amount of EHDP is between 0.5 to 5 wt. % of the electrolyte. It is preferable that the amount of HPCP is between 0.5 to 5 wt. % of the electrolyte. Preferably, the amount of DOPO-HQ is less than or equal to 1.5 wt. % of the electrolyte. More preferably, the amount of PFPN is 0.5 to 2.9 wt. % of the electrolyte. Yet more preferably, the non-aqueous organic solvent comprises carbonate-based organic solvents. In a preferred embodiment, the carbonate-based organic solvents is selected from a group consisting of ethylene carbonate (EC), ethyl methyl carbonate (EMC), diethyl carbonate (DEC), Propylene carbonate (PC), dimethyl carbonate (DMC) and a mixture thereof. Preferably, the film former is selected from a group consisting of vinylene carbonate (VC) and fluoroethylene carbonate (FEC). More preferably, the lithium salt comprises lithium hexafluorophosphate ($LiPF_6$).

In another aspect of the invention, there is provided an electrolyte for a lithium-ion battery comprising: a lithium salt, a non-aqueous organic solvent which includes a carbonate-based solvent, a flame retardant, a film former and a stabilizing medium, wherein the flame retardant comprises $PYR_{1R}PF_6$ (N-Methyl-N-alkylpyrrolidinium Hexafluorophosphate Salt), the stabilizing medium includes first, second and third stabilizers. Preferably, the lithium salt comprises $LiPF_6$; the carbonate-based organic solvents is selected from a group consisting of ethylene carbonate (EC), ethyl methyl carbonate (EMC), diethyl carbonate (DEC), Propylene carbonate (PC), dimethyl carbonate (DMC) and a mixture thereof; the film former is selected from a group consisting of vinylene carbonate (VC) and fluoroethylene carbonate (FEC); the $PYR_{1R}PF_6$ indicates the number of carbon atoms in the alkyl side chains, in which R is selected from any one of 2 to 10; the first stabilizer is selected from a group consisting of bis(xoalateborate ($BOB^-$), difluoro (oxalate)borate ($ODFB^-$) and bis(mandelato)borate($BMB^-$); the second stabilizer comprises an ionic liquid with an anion selected from a group consisting of $TFSI^-$ and $FSI^-$; and the third stabilizer is selected from a group consisting of Ethoxy (pentafluoro) cyclotriphosphazene (PFPN), Ethylhexyl Diphenyl Phosphate (EHDP), Hexaphenoxycyclotriphosphazene (HPCP) and 10 (2,5-dihydroxyphenyl)-9,10-dihydro-9-oxa-10-phosphaphenanthrene-10-oxide (DOPO-HQ). More preferably, the flame retardant is $PYR_{16}PF_6$; the first stabilizer is $PYR_{14}BOB$; the second stabilizer is $PYR_{14}TFSI$ at a ratio of 1:0.5:1 wt %. It is preferable that the flame retardant is $PYR_{16}PF_6$; the first stabilizer is $PYR_{14}ODFB$; the second stabilizer is $PYR_{13}TFSI$ at a ratio of 1:0.5:1 wt %. Preferably, the flame retardant is $PYR_{16}PF_6$; the first stabilizer is $PYR_{14}ODFB$; the second stabilizer is $PYR_{13}TFSI$ at a ratio of 10:1:4 wt %. Yet more preferably, the carbonate-based organic solvent comprises EC, DMC and DEC at 1:1:1 vol % and the film former comprises 3.5 wt % of VC.

In a further aspect of the invention, there is provided a battery comprising:

a positive electrode, a negative electrode, a separator, and an electrolyte as claimed in any one of claims 1 to 30. Preferably, the positive electrode comprises $LiFePO_4$. More preferably, the negative electrode is formed from a material selected from a group consisting of carbon and carbon/silicon (SiC). Yet more preferably, the separator is a composite film formed from a material selected from a group consisting of Polypropylene (PP), Polyethylene (PE), ceramic, glass fiber and a combination thereof.

BRIEF DESCRIPTION OF DRAWINGS

The invention will now be more particularly described, by way of example only, with reference to the accompanying drawings, in which:

FIG. 1 is table showing the synthesis of $PYR_{12}Br$, $PYR_{13}Br$, $PYR_{14}Br$, $PYR_{15}Br$, $PYR_{16}Br$, $PYR_{17}Br$, $PYR_{18}Br$, $PYR_{19}Br$, $PYR_{110}Br$;

FIG. 3 is a table showing the side reaction test results of $PYR_{12}PF_6$, $PYR_{13}PF_6$, $PYR_{14}PF_6$, $PYR_{15}PF_6$, $PYR_{16}PF_6$, $PYR_{17}PF_6$, $PYR_{18}PF_6$, $PYR_{19}PF_6$ and $PYR_{110}PF_6$ as the flame retardant in the ionic liquid (IL) at 5 wt %, 10 wt %, 15 wt % and 20 wt % with organic electrolyte (OE) 1M $LiPF_6$ with ethylene carbonate (EC)/dimethyl carbonate (DMC)/diethyl carbonate (DECX1:1:1 vol %)+3.5 wt % vinylene carbonate (VC) at 95 wt %, 90 wt %, 85 wt % and 80 wt %;

FIG. 7 is a table showing the 0.2 C charge and discharge life cycle of a Negative A and Negative B electrodes of a battery with electrolyte comprises 1M $LiPF_6$ with ethylene carbonate (EC)/dimethyl carbonate (DMC)/diethyl carbonate (DEC)(1:1:1 vol %)+3.5 wt % vinylene carbonate (VC) alone or with $PYR_{12}PF_6$, $PYR_{13}PF_6$, $PYR_{14}PF_6$, $PYR_{15}PF_6$, $PYR_{16}PF_6$, $PYR_{17}PF_6$, $PYR_{18}PF_6$, $PYR_{19}PF_6$ and/or $PYR_{110}PF_6$ in various proportions, FIG. 8 is a table showing 0.2 C charge and discharge life cycle of a Negative A and Negative B electrodes of a battery with electrolyte comprises 1M $LiPF_6$ with ethylene carbonate (EC)/dimethyl carbonate (DMC)/diethyl carbonate (DEC)(1:1:1 vol %)+3.5 wt % vinylene carbonate (VC) alone or with $PYR_{12}PF_6$, $PYR_{15}PF_6$, $PYR_{16}PF_6$, and the addition of a first stabilizer $PYR_{14}BOB$, $PYR_{14}ODFB$ or $PYR_{14}BMB$ in various proportions;

FIG. 9 is a table showing 0.2 C charge and discharge life cycle of a battery with a Negative A electrode in an electrolyte comprises 1M $LiPF_6$ with ethylene carbonate (EC)/dimethyl carbonate (DMC)/diethyl carbonate (DEC)(1:1:1 vol %)+3.5 wt % vinylene carbonate (VC) alone or with $PYR_{15}PF_6$, and the addition of a first stabilizer $PYR_{14}BOB$ or $PYR_{14}ODFB$ and a second stabilizer $PYR_{14}TFSI$ or $PYR_{14}FSI$ in various proportions and a Negative B electrode in an electrolyte comprises 1M $LiPF_6$ with ethylene carbonate (EC)/dimethyl carbonate (DMC)/diethyl carbonate (DEC)(1:1:1 vol %)+3.5 wt % fluoroethylene carbonate (FEC) alone or with $PYR_{15}PF_6$, and the addition of a first stabilizer $PYR_{14}BOB$ or $PYR_{14}ODFB$ and a second stabilizer $PYR_{14}TFSI$ or $PYR_{14}FSI$ in various proportions;

FIG. 10 is a table showing 0.2 C charge and discharge life cycle of a battery with a Negative A electrode in an electrolyte comprises 1M $LiPF_6$ with ethylene carbonate (EC)/dimethyl carbonate (DMC)/diethyl carbonate (DEC)(1:1:1 vol %)+3.5 wt % vinylene carbonate (VC) (OE) alone or with $PYR_{16}PF_6$, $PYR_{14}BOB$, $PYR_{14}TSFI$ at the ratio of (10:1:4 wt %) (IL) or an electrolyte comprises OE, IL and a third stabilizer Ethoxy(pentafluoro) cyclotriphosphazene (PFPN), Ethylhexyl Diphenyl Phosphate (EHDP), Hexaphenoxycyclotriphosphazene (HPCP) or 10-(2,5-dihydroxyphenyl)-9,10-dihydro-9-oxa-10-phosphaphenanthrene-10-oxide (DOPO-HQ) in various amount;

FIG. 11 is a table showing the side reaction testing result with electrolyte comprises of 1M $LiPF_6$ with ethylene carbonate (EC)/dimethyl carbonate (DMC)/diethyl carbonate (DEC)(1:1:1 vol %)+3.5 wt % vinylene carbonate (VC)

Figure 12:
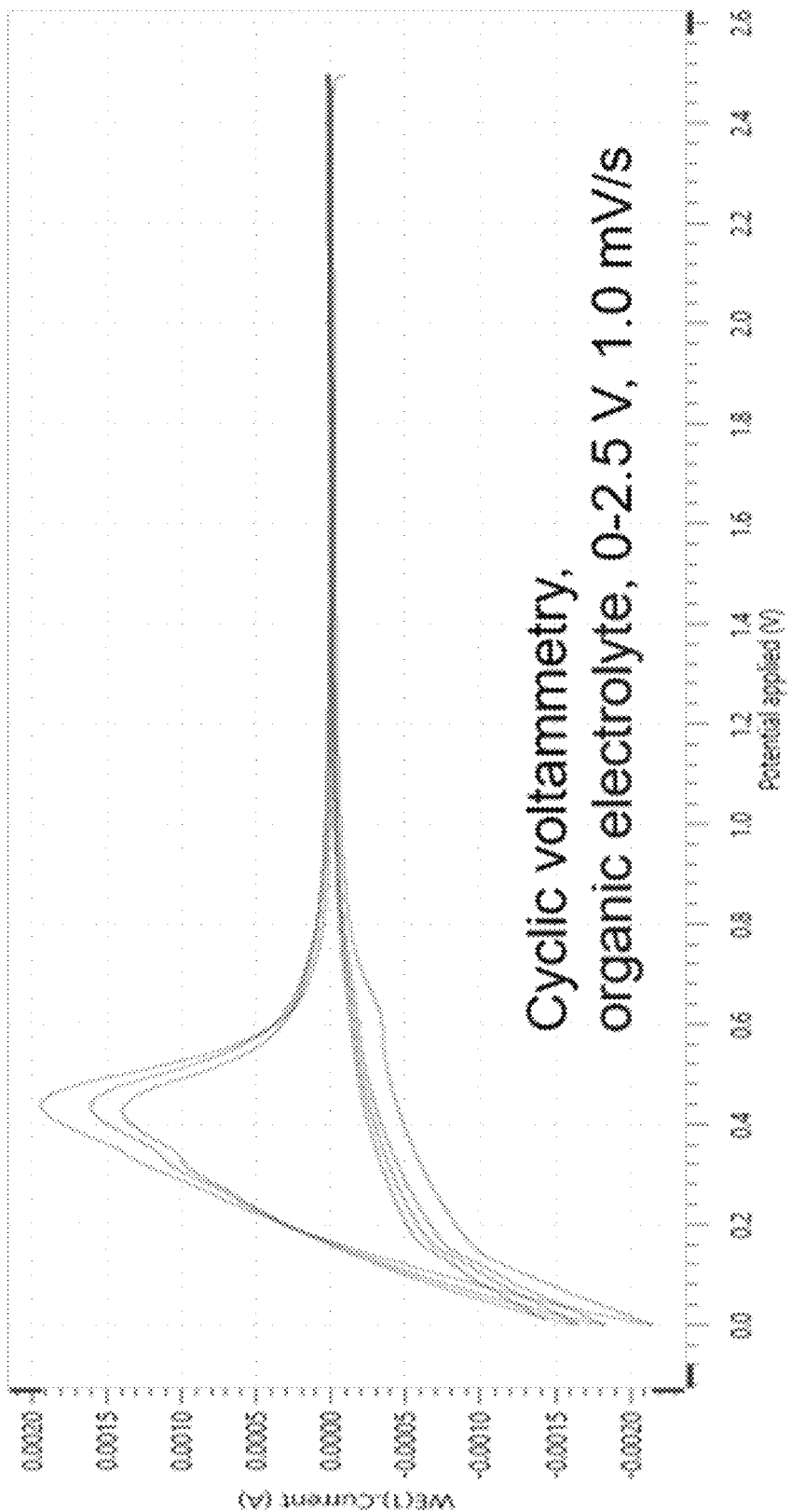
Figure 13:
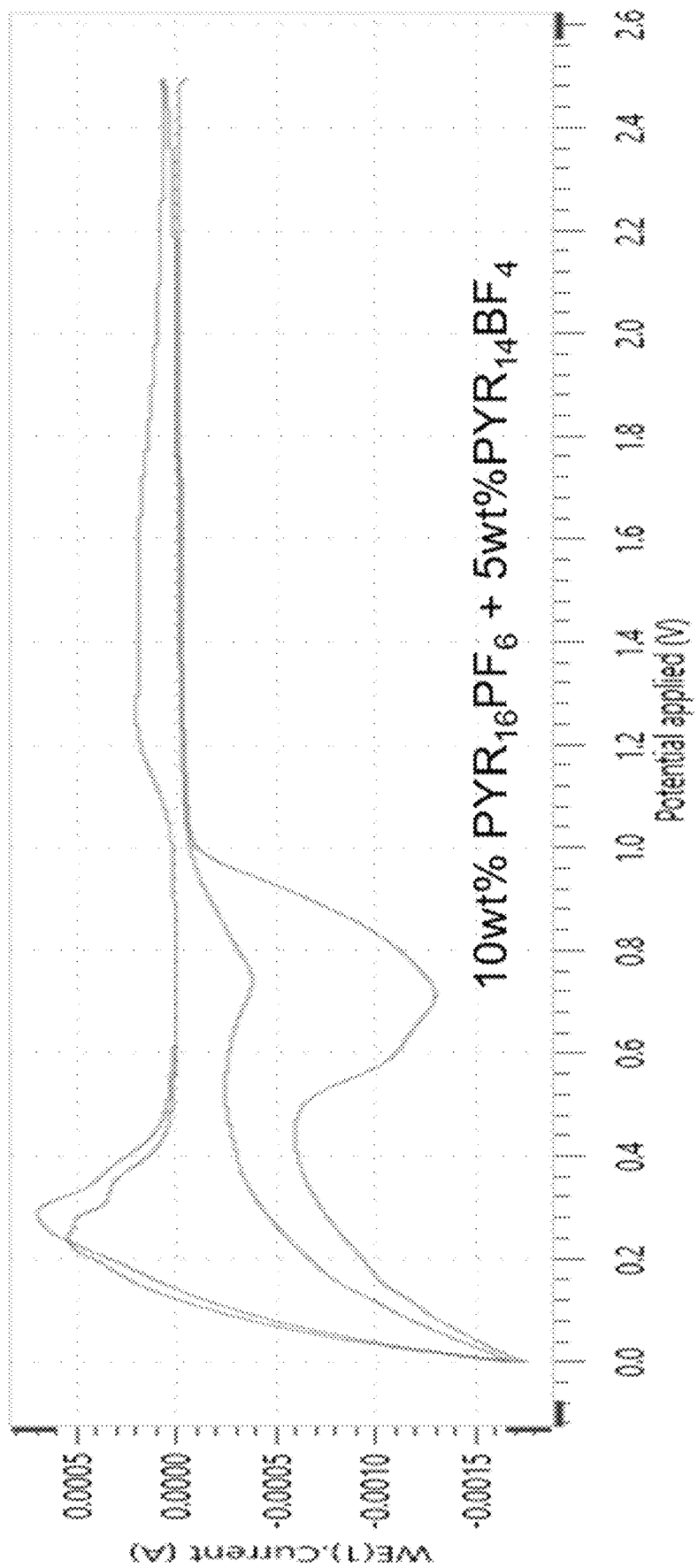
Figure 14:
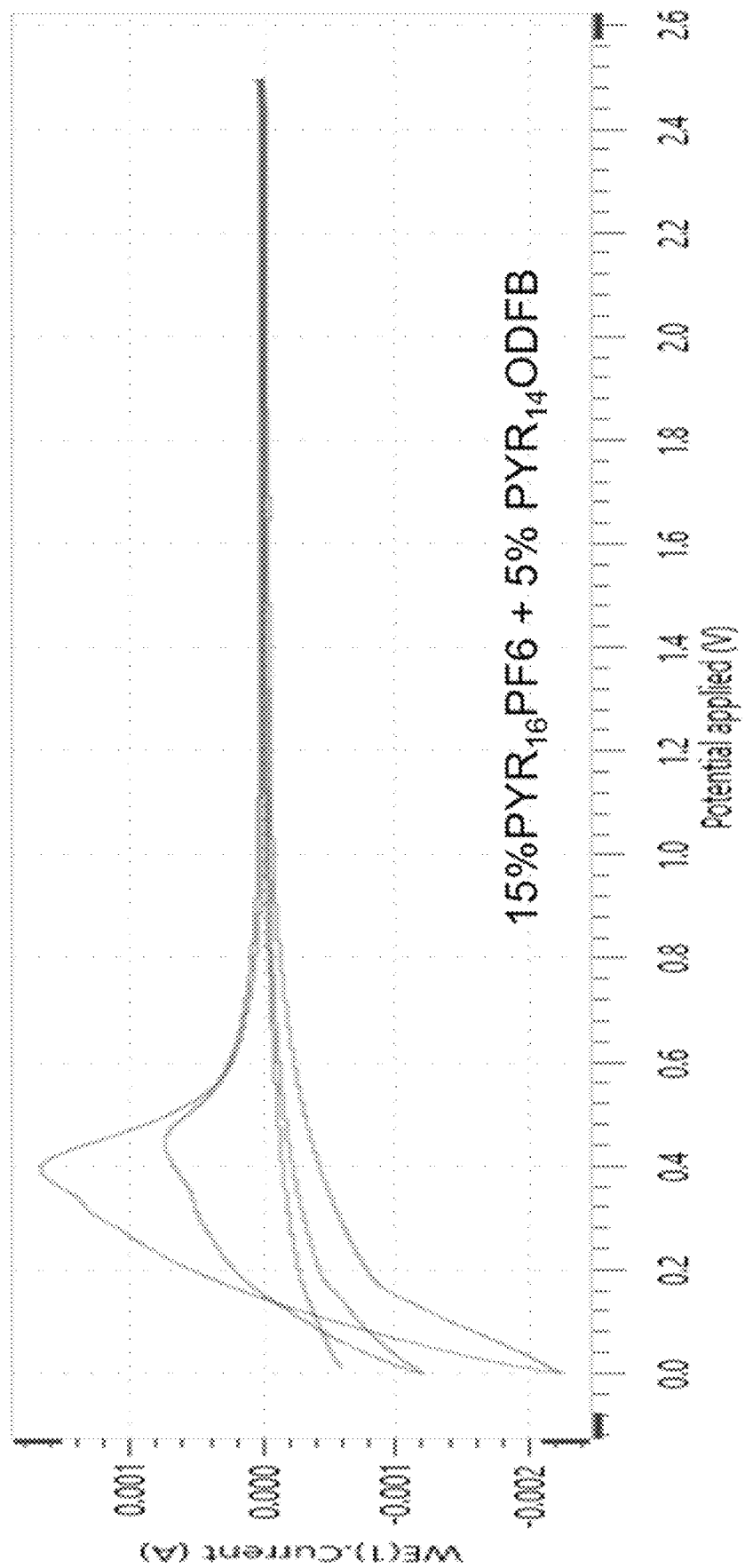
Figure 15:
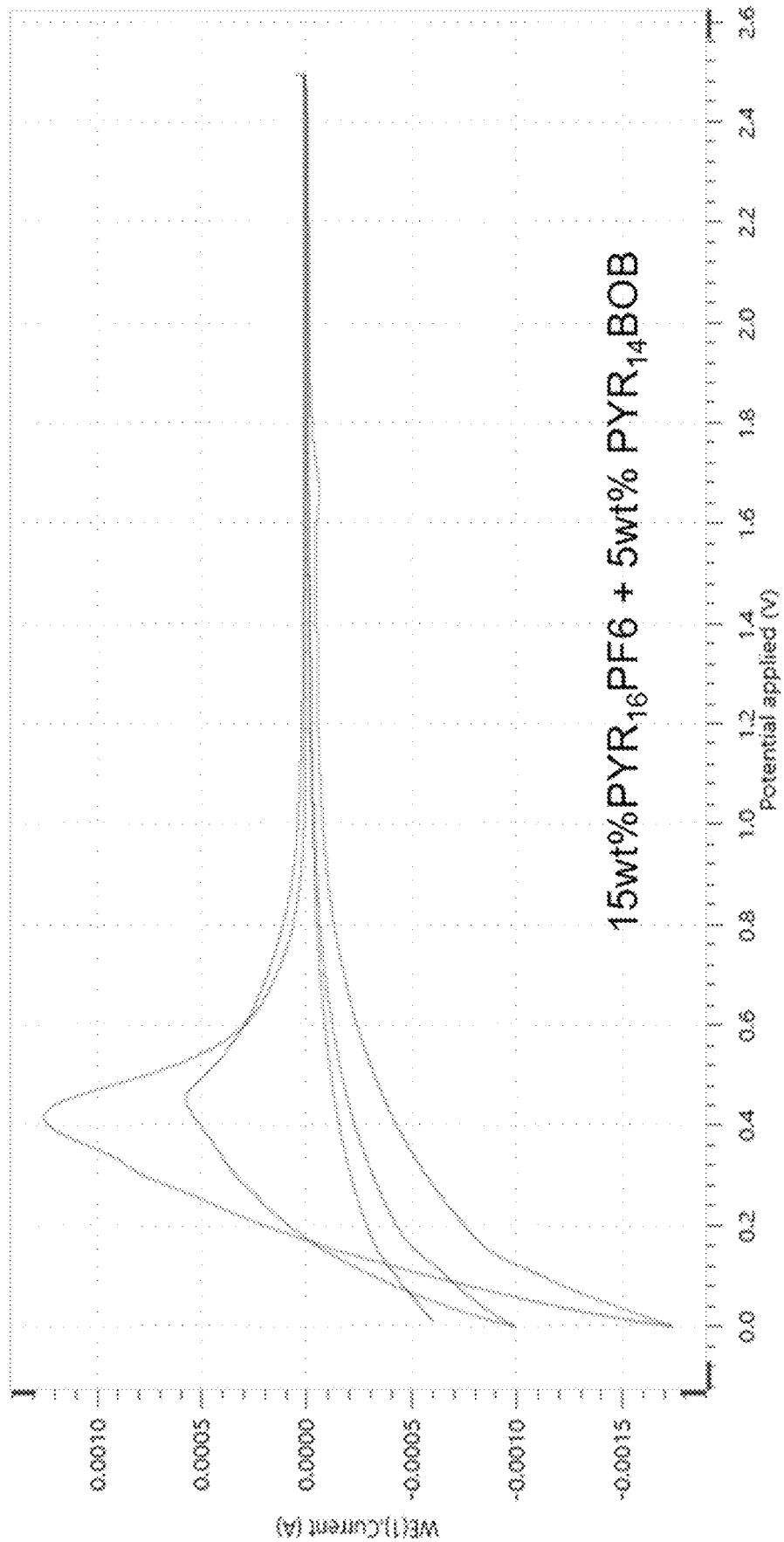
Figure 16:
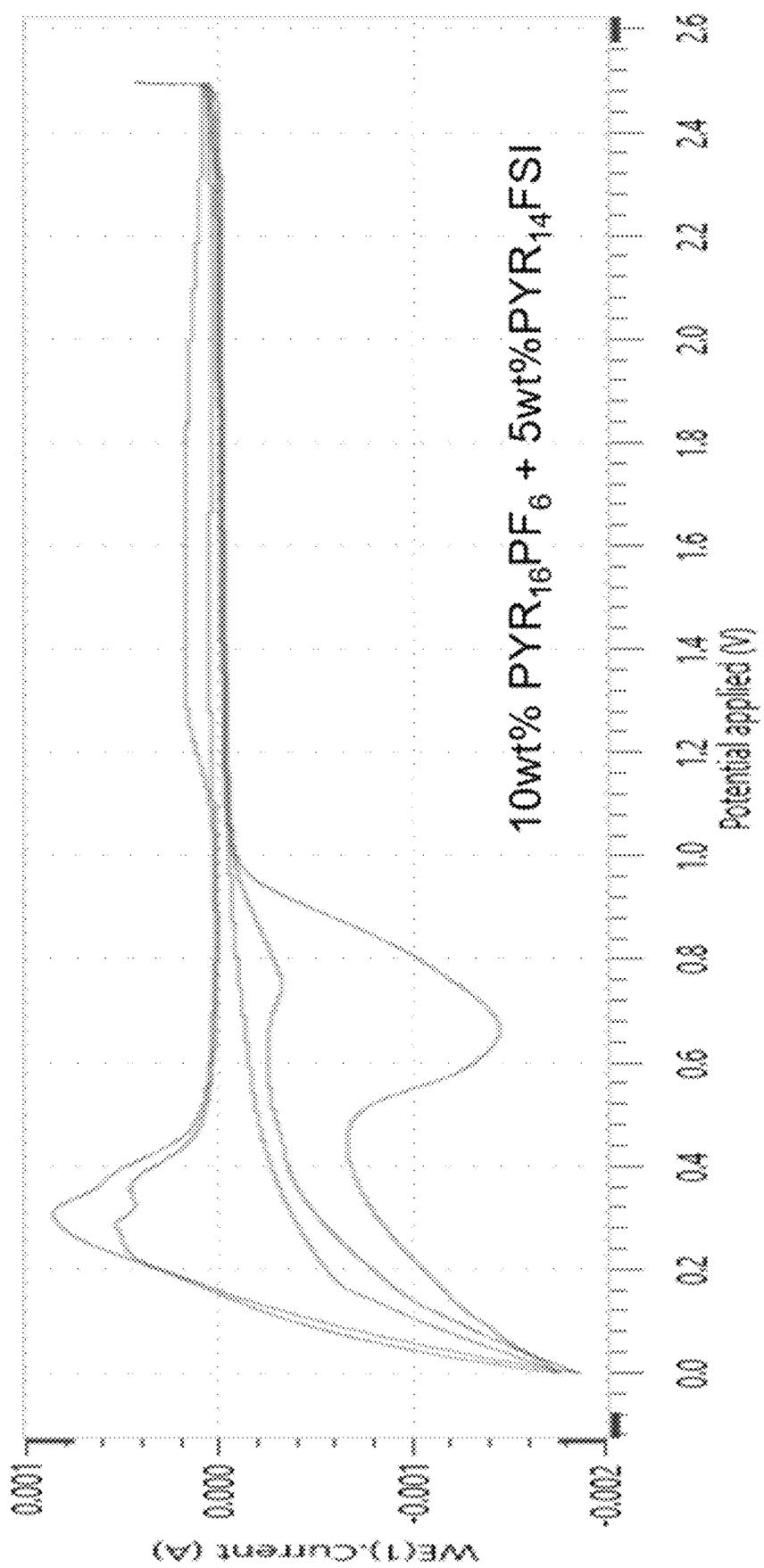
Figure 17:
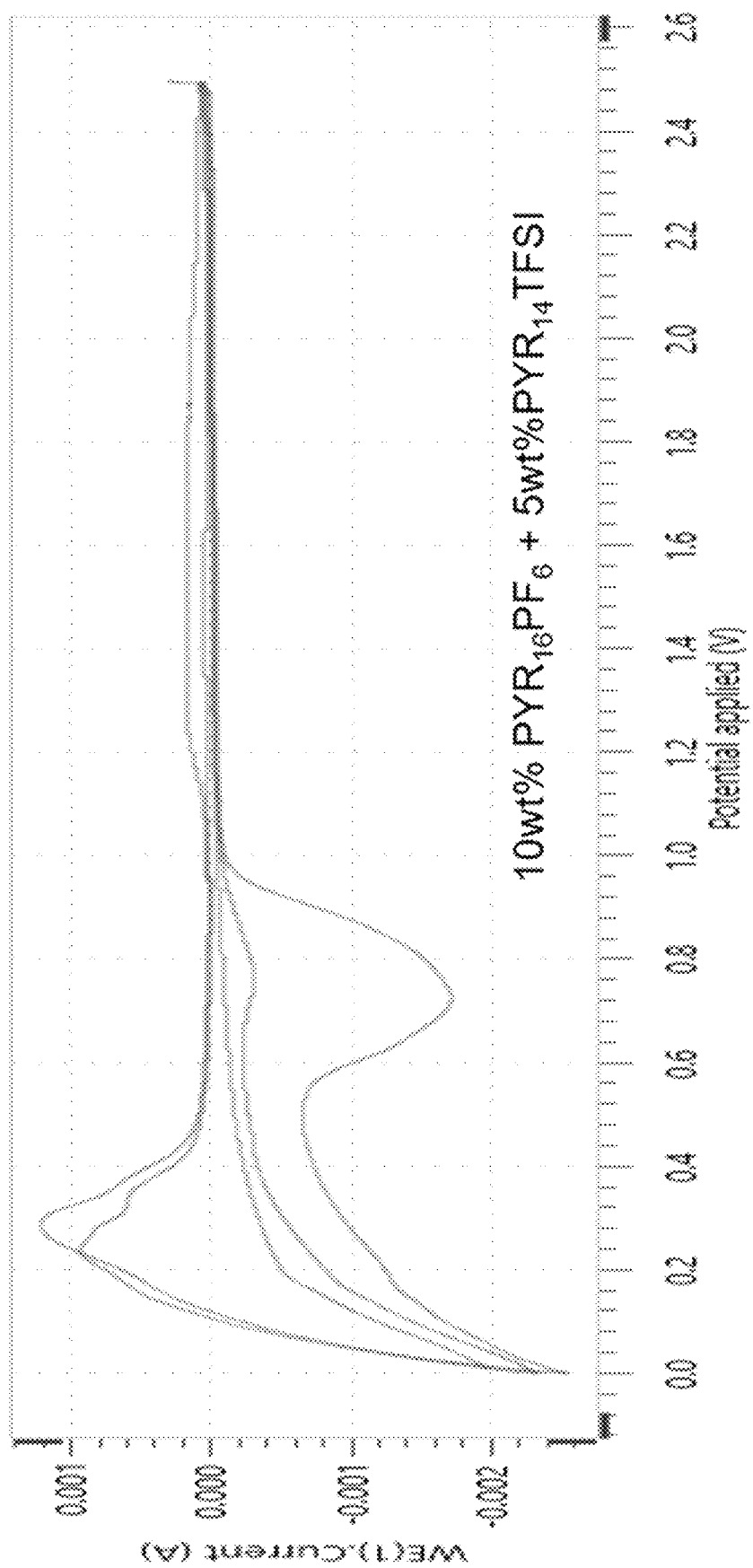
Figure 18:
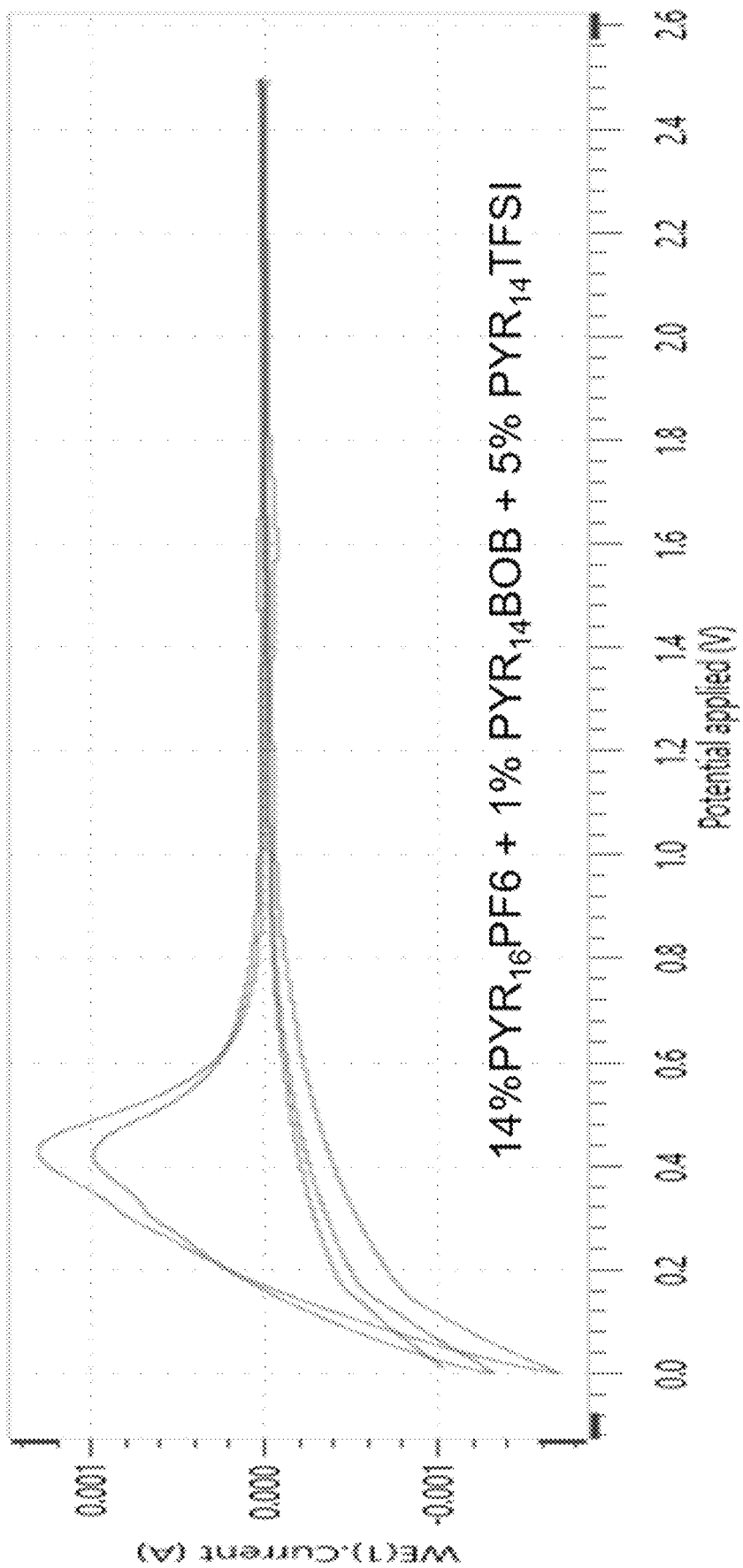
Figure 19:
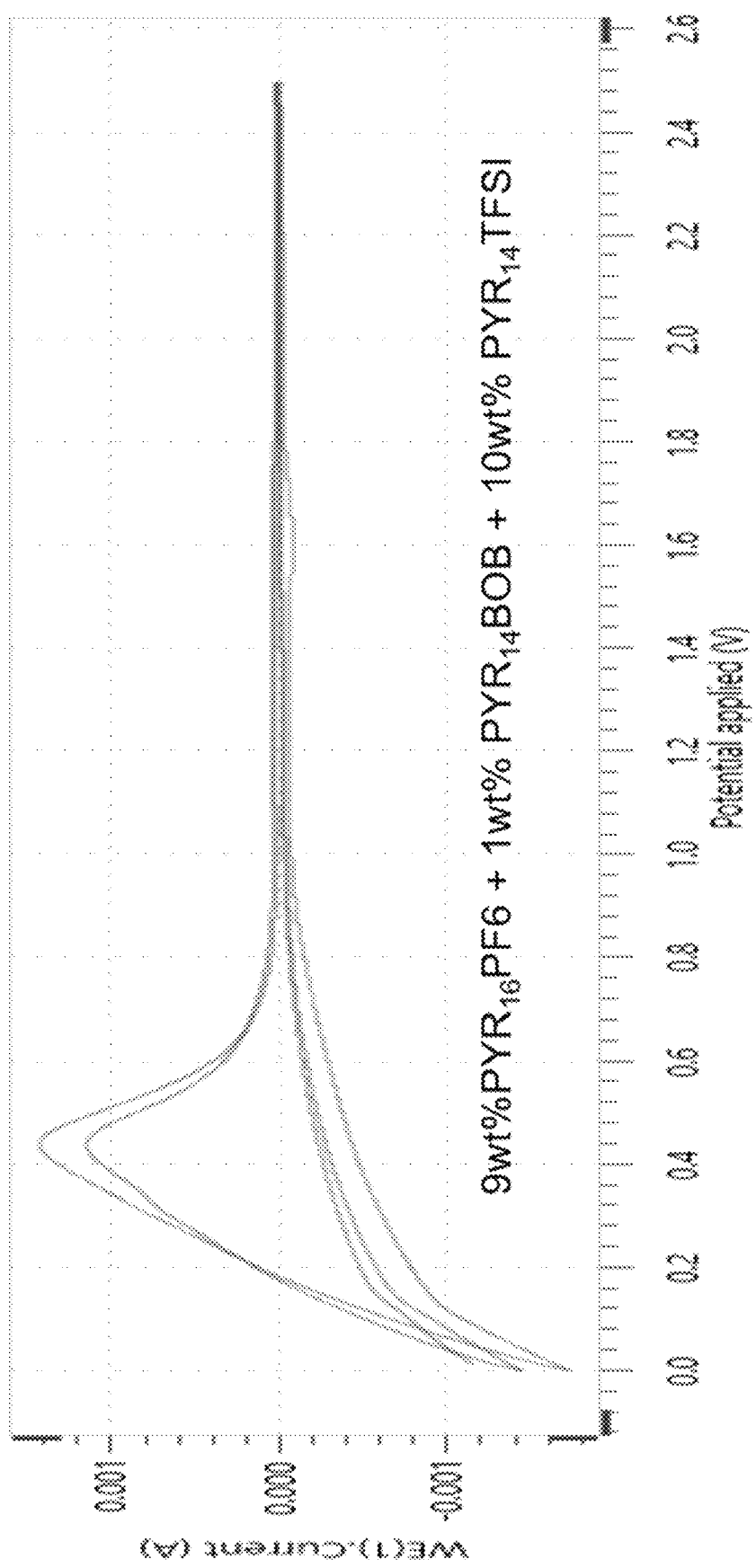

(OE) alone or with flame retardant and a first stabilizer, or OE with flame retardant and second stabilizer or OE with flame retardant, first and second stabilizer;

FIG. 12 is a cyclic voltammetry line graph at 0-2.5V at 1.0 mV/s showing no side reaction measurable on the battery with electrolyte comprises 100 wt % of 1M LiPF$_6$ with ethylene carbonate (EC)/dimethyl carbonate (DMC)/diethyl carbonate (DEC)(1:1:1 vol %)+3.5 wt % vinylene carbonate (VC);

FIG. 13 is a cyclic voltammetry line graph showing side reaction measurable at 0.5-1.0 V on the battery with electrolyte comprises 85 wt % of 1M LiPF$_6$ with ethylene carbonate (EC)/dimethyl carbonate (DMC)/diethyl carbonate (DEC)(1:1:1 vol %)+3.5 wt % vinylene carbonate (VC), 10 wt % of PYR$_{16}$PF$_6$ and 5 wt % PYR$_{14}$BF$_4$;

FIG. 14 is a cyclic voltammetry line graph showing no side reaction measurable on the battery with electrolyte comprises 80% of 1M LiPF$_6$ with ethylene carbonate (EC)/dimethyl carbonate (DMC)/diethyl carbonate (DEC)(1:1:1 vol %)+3.5 wt % vinylene carbonate (VC), 15 wt % of PYR$_{16}$PF$_6$ and 5 wt % PYR$_{14}$ODFB;

FIG. 15 is a cyclic voltammetry line graph showing no side reaction measurable on the battery with electrolyte comprises 80% of 1M LiPF$_6$ with ethylene carbonate (EC)/dimethyl carbonate (DMC)/diethyl carbonate (DEC)(1:1:1 vol %)+3.5 wt % vinylene carbonate (VC), 15 wt % of PYR$_{16}$PF$_6$ and 5 wt % PYR$_{14}$BOB;

FIG. 16 is a cyclic voltammetry line graph showing side reaction measurable at 0.4-1.0 V on the battery with electrolyte comprises 85% of 1M LiPF$_6$ with ethylene carbonate (EC)/dimethyl carbonate (DMC)/diethyl carbonate (DEC)(1:1:1 vol %)+3.5 wt % vinylene carbonate (VC), 10 wt % of PYR$_{16}$PF$_6$ and 5 wt %, PYR$_{14}$FSI;

FIG. 17 is a cyclic voltammetry line graph showing side reaction measurable at 0.5-1.0 V on the battery with electrolyte comprises 85% of 1M LiPF$_6$ with ethylene carbonate (EC)/dimethyl carbonate (DMC)/diethyl carbonate (DEC)(1:1:1 vol %)+3.5 wt % vinylene carbonate (VC), 10 wt % of PYR$_{16}$PF$_6$ and 5 wt % PYR$_{14}$TFSI;

FIG. 18 is a cyclic voltammetry line graph showing no side reaction measurable on the battery with electrolyte comprises 80% of 1M LiPF$_6$ with ethylene carbonate (EC)/dimethyl carbonate (DMC)/diethyl carbonate (DEC)(1:1:1 vol %)+3.5 wt % vinylene carbonate (VC), 14 wt % of PYR$_{16}$PF$_6$, 1 wt % of PYR$_{14}$BOB and 5 wt % PYR$_{14}$TFSI;

FIG. 19 is a cyclic voltammetry line graph showing no side reaction measurable on the battery with electrolyte comprises 80% of 1M LiPF$_6$ with ethylene carbonate (EC)/dimethyl carbonate (DMC)/diethyl carbonate (DEC)(1:1:1 vol %)+3.5 wt % vinylene carbonate (VC), 9 wt % of PYR$_{16}$PF$_6$, 1 wt % of PYR$_{14}$BOB and 10 wt % PYR$_{14}$TFSI; and FIG. 20 is a table showing 0.2 C charge and discharge life cycle of Electrode A in a battery with an electrolyte comprises 1M LiPF$_6$ with ethylene carbonate (EC)/dimethyl carbonate (DMC)/diethyl carbonate (DEC)(1:1:1 vol %)+3.5 wt % vinylene carbonate (VC) (OE) alone or with PYR$_{16}$PF$_6$, PYR$_{14}$BOB, PYR$_{14}$TSFI at the ratio of 1:0.5:1 wt % ionic liquid (IL) or an electrolyte comprises OE, IL and a third stabilizer Ethoxy(pentafluoro) cyclotriphosphazene ((PFPN), Ethylhexyl Diphenyl Phosphate (EHDP), Hexaphenoxycyclotriphosphazene (HPCP) or 10-(2,5-dihydroxyphenyl)-9,10-dihydro-9-oxa-10-phosphaphenanthrene-10-oxide (DOPO-HQ) in various amount.

FIG. 21 is a table showing 0.2 C charge and discharge life cycle of Electrode A in a battery with an electrolyte comprises 1M LiPF$_6$ with ethylene carbonate (EC)/dimethyl carbonate (DMC)/diethyl carbonate (DEC)(1:1:1 vol %)+3.5 wt % vinylene carbonate (VC) (OE) alone or with PYR$_{16}$PF$_6$, PYR$_{14}$ODFB, PYR$_{13}$TSFI at the ratio of 1:0.5:1 wt % ionic liquid (IL) or an electrolyte comprises OE, IL and a third stabilizer Ethoxy(pentafluoro) cyclotriphosphazene ((PFPN), Ethylhexyl Diphenyl Phosphate (EHDP), Hexaphenoxycyclotriphosphazene (HPCP) or 10-(2,5-dihydroxyphenyl)-9,10-dihydro-9-oxa-10-phosphaphenanthrene-10-oxide (DOPO-HQ) in various amount.

FIG. 22 is a table showing 0.2 C charge and discharge life cycle of Electrode A in a battery with an electrolyte comprises 1M LiPF$_6$ with ethylene carbonate (EC)/dimethyl carbonate (DMC)/diethyl carbonate (DEC)(1:1:1 vol %)+3.5 wt % vinylene carbonate (VC) (OE) alone or with PYR$_{16}$PF$_6$, PYR$_{14}$ODFB, PYR$_{13}$TSFI at the ratio of 10:1:4 wt % ionic liquid (IL) or an electrolyte comprises OE, IL and a third stabilizer Ethoxy(pentafluoro) cyclotriphosphazene ((PFPN), Ethylhexyl Diphenyl Phosphate (EHDP), Hexaphenoxycyclotriphosphazene (HPCP) or 10-(2,5-dihydroxyphenyl)-9,10-dihydro-9-oxa-10-phosphaphenanthrene-10-oxide (DOPO-HQ) in various amount.

DETAILED DESCRIPTION OF PREFERRED EMBODIMENT

PYR$_{1R}$PF$_6$ series ionic liquid is an identified candidate that offers an alternative to room temperature ionic liquids because it has a relatively high melting point. PYR$_{1R}$PF$_6$ series ionic liquid also possesses the advantages of relatively low volatility and relatively high non-flammability. Proton solvents must be used in combination with PYR$_{1R}$PF$_6$ series ionic liquid at room temperature because PYR$_{1R}$PF$_6$ is in solid state at room temperature due to its relatively high melting point. The PF$_6^-$ increases the fire retardancy of the ionic liquid and hence acts as a tire retardant Some of the PYR$_{1R}$PF$_6$ series ionic liquid that are considered more suitable are each mixed with a carbonate electrolyte to be used in a lithium iron phosphate(LFP) battery for electrical performance testing. Although charging and discharging are possible or can be performed, lithium deposition occurs slowly over charging and discharging of the battery. The deposition lowers the number of battery cycles to be less than 100 times, hence the battery cannot be commercialized With reference to FIGS. 1 to 20, the following findings offer a solution that mitigates all of the aforementioned shortcomings More specifically, the present invention offers a novel electrolyte formulation containing a PYR$_{1R}$PF$_6$ series ionic liquid for use in a commercializable lithium ion battery.

Below are the method of synthesis of certain PYR$_{1R}$PF$_6$ series ionic liquid.

Synthesis of N-methyl-N-alkylpyrrolidinium PYR$_{1R}^+$ cation PF$_6^-$ anion is a two-step synthesis. With reference to FIG. 1 the synthesis of PYR$_{12}$PF$_6$, PYR$_3$PF$_6$, PYR$_{14}$PF$_6$, PYR$_{15}$PF$_6$, PYR$_{16}$PF$_6$, PYR$_{17}$PF$_6$, PYR$_{18}$PF$_6$, PYR$_{19}$PF$_6$ and PYR$_{110}$PF$_6$ are provided in detail below.

Step 1—Synthesis of PYR$_{12}$Br, PYR$_{13}$Br, PYR$_{14}$Br, PYR$_{15}$Br, PYR$_{16}$Br, PYR$_{17}$Br, PYR$_{18}$Br, PYR$_{19}$Br, PYR$_{110}$Br The synthesis of N-ethyl-N-methylpyrrolidinium bromide (PYR$_{12}$Br)

N-methylpyrrolidine (NMPD) is purified by distillation at 85° C. The purified N-methylpyrrolidine and N-ethyl bromide (n-bromoethane) are mixed at a molar ratio of 1:1.1, followed by adding an equal volume of deionized water with n-bromoethane, and mixing and stirring in a 5 degree Celsius ice bath. After 2 hours, the supernatant was N-ethyl-N-methylpyrrolidinium bromide ($PYR_{12}Br$).

The Synthesis of N-propyl-N-methylpyrrolidinium bromide ($PYR_{13}Br$)

N-methylpyrrolidine (NMPD) is purified by distillation at 85° C. The purified N-methylpyrrolidine and N-propyl bromide are mixed at a molar ratio of 1:1.1, followed by adding an equal volume of deionized water with n-bromopropane, and mixing and stirring in a 10 degree Celsius ice bath. After 2 hours, the supernatant was N-propyl-N-methylpyrrolidinium bromide ($PYR_{13}Br$).

The Synthesis of N-butyl-N-methylpyrrolidinium bromide ($PYR_{14}Br$)

N-methylpyrrolidine (NMPD) is purified by distillation at 85° C. The purified N-methylpyrrolidine and N-butyl bromide are mixed at a molar ratio of 1:1.1, followed by adding an equal volume of deionized water with n-bromobutane, and mixing and stirring in a 10 degree Celsius ice bath. After 2 hours, the supernatant was N-butyl-N-methylpyrrolidinium bromide ($PYR_{14}Br$).

The Synthesis of N-pentyl-N-methylpyrrolidinium bromide ($PYR_{15}Br$)

N-methylpyrrolidine (NMPD) is purified by distillation at 85° C. The purified N-methylpyrrolidine and N-pentyl bromide are mixed at a molar ratio of 1:1.1, followed by adding an equal volume of deionized water with n-bromopantane, and mixing and stirring in a 60 degree Celsius hot bath. After 2 hours, the supernatant was N-pentyl-N-methylpyrrolidinium bromide ($PYR_{15}Br$).

The Synthesis of N-hexyl-N-methylpyrrolidinium bromide ($PYR_{16}Br$)

N-methylpyrrolidine (NMPD) is purified by distillation at 85° C. The purified N-methylpyrrolidine and N-hexyl bromide are mixed at a molar ratio of 1:1.1, followed by adding an equal volume of deionized water with n-bromohexane, and mixing and stirring in a 60 degree Celsius hot bath. After 2 hours, the supernatant was N-hexyl-N-methylpyrrolidinium bromide ($PYR_{16}Br$).

The Synthesis of N-heptyl-N-methylpyrrolidinium bromide ($PYR_{17}Br$)

N-methylpyrrolidine (NMPD) is purified by distillation at 85° C. The purified N-methylpyrrolidine and N-heptyl bromide are mixed at a molar ratio of 1:1.1, followed by adding an equal volume of deionized water with n-bromoheptane, and mixing and stirring in a 70 degree Celsius hot bath. After 2 hours, the supernatant was N-heptyl-N-methylpyrrolidinium bromide ($PYR_{17}Br$).

The synthesis of N-octyl-N-methylpyrrolidinium bromide ($PYR_{18}Br$)

N-methylpyrrolidine (NMPD) is purified by distillation at 85° C. The purified N-methylpyrrolidine and N-octyl bromide are mixed at a molar ratio of 1:1.1, followed by adding an equal volume of deionized water with n-bromooctane, and mixing and stirring in a 70 degree Celsius hot bath. After 2 hours, the supernatant was N-octyl-N-methylpyrrolidinium bromide ($PYR_{19}Br$).

The synthesis of N-nonyl-N-methylpyrrolidinium bromide ($PYR_{19}Br$)

N-methylpyrrolidine (NMPD) is purified by distillation at 85° C. The purified N-methylpyrrolidine and Bromononame are mixed at a molar ratio of 1:1.1, followed by adding an equal volume of deionized water with bromononame, and mixing and stirring in a 70 degree Celsius hot bath. After 2 hours, the supernatant was N-nonyl-N-methylpyrrolidinium bromide ($PYR_{19}Br$).

The synthesis of N-decyl-N-methylpyrrolidinium bromide ($PYR_{110}Br$)

N-methylpyrrolidine (NMPD) is purified by distillation at 85° C. The purified N-methylpyrrolidine and Bromodecane are mixed at a molar ratio of 1:1.1, followed by adding an equal volume of deionized water with n-bromodecane, and mixing and stirring in a 70 degree Celsius hot bath. After 2 hours, the supernatant was N-decyl-N-methylpyrrolidinium bromide ($PYR_{110}Br$).

Step 2—Synthesis of Pyrrolidinium Ionic Liquids $PYR_{12}PF_6$, $PYR_{13}PF_6$, $PYR_{14}PF_6$, $PYR_{15}PF_6$, $PYR_{16}PF_6$, $PYR_{17}PF_6$, $PYR_{18}PF_6$, $PYR_{19}PF_6$, and $PYR_{110}PF_6$

Synthesis Method of N-ethyl-N-methylpyrrolidinium hexafluorophosphate ($PYR_{12}PF_6$)

Adding the N-ethyl-N-methylpyrrolidinium bromide salt synthesized in Step 1 to a molar amount (1M) of potassium hexafluorophosphate($KPF_6$), followed by addition of deionized water. The ratio of deionized water to the bromine salt is 1:1 wt. %, stirred at room temperature until reaction is completed. The white precipitate is filtered and is placed in a container. Deionized water is added to wash the white precipitate which is then filtered out. The white precipitate is washed for three times. The white precipitate is then dried in a 60 degree vacuum oven until it reaches a moisture content of 20 ppm or less.

Synthesis Method of N-propyl-N-methylpyrrolidinium hexafluorophosphate ($PYR_{13}PF_6$)

The N-propyl-N-methylpyrrolidinium bromide synthesized in Step 1 was added to a molar amount (1M) of potassium hexafluorophosphate($KPF_6$), followed by addition of deionized water. The ratio of deionized water to the bromine salt is 1:1 wt. %. The mixture is stirred at room temperature until reaction is completed, the resulting white precipitate is filtered and is placed in a container. Deionized water is added to wash the white precipitate which is then filtered out. The white precipitate is washed for three times. The cleaned precipitate is dried in a 60 degree vacuum oven until it reaches a moisture content of 20 ppm or less.

Synthesis Method of N-butyl-N-methylpyrrolidinium hexafluorophosphate ($PYR_{14}PF_6$)

The N-butyl-N-methylpyrrolidinium bromide synthesized in Step 1 is added to a molar amount (1M) of potassium hexafluorophosphate(KPF$_6$), followed by an addition of deionized water. The ratio of deionized water to the bromine salt is 1:1 wt. %. The mixture is stirred at room temperature until reaction is completed. The white precipitate is filtered and placed in a container. Deionized water is added to wash the white precipitate which is then filtered. The white precipitate is cleaned three times and is then dried in a 60 degree vacuum oven until it reaches a moisture content of 20 ppm or less.

Synthesis Method of N-pentyl-N-methylpyrrolidinium hexafluorophosphate (PYR$_{15}$PF$_6$)

The N-pentyl-N-methylpyrrolidinium bromide synthesized in Step 1 is added to a molar amount (1M) of potassium hexafluorophosphate(KPF$_6$), followed by addition of deionized water. The ratio of deionized water to the bromine salt is 1:1 wt. %. The mixture is stirred at room temperature until reaction is completed. The white precipitate is then filtered out and is placed in a container. deionized water is added for washing and the white precipitate is filtered out. The washing process is repeated three times. The precipitate is then dried in a 60 degree vacuum oven until the moisture content is of 20 ppm or less.

Synthesis Method of N-hexyl-N-methylpyrrolidinium hexafluorophosphate (PYR$_6$PF$_6$)

The N-hexyl-N-methylpyrrolidinium bromide synthesized in Step 1 is added to a molar amount (1M) of potassium hexafluorophosphate(KPF$_6$), followed by addition of deionized water. The ratio of deionized water to the bromine salt is 1:1 wt. %. The mixture is stirred at room temperature until reaction is completed. The resulting white precipitate is filtered and is placed in a container. Deionized water is added to wash the white precipitate which is then filtered out. The washing process is repeated three times. Finally, the resulting white precipitate is dried in a 60 degree vacuum oven to a moisture content of 20 ppm or less.

Synthesis Method of N-heptyl-N-methylpyrrolidinium hexafluorophosphate (PYR$_{17}$PF$_6$)

The N-heptyl-N-methylpyrrolidinium bromide synthesized in Step 1 is added to a molar amount (1M) of potassium hexafluorophosphate(KPF$_6$), followed by addition of deionized water. The ratio of deionized water to the bromine salt is 1:1 wt. %. The mixture is stirred at room temperature until reaction is completed. The resulting the white precipitate is filtered. The white precipitate is removed and placed in a container. Deionized water is added for washing and the white precipitate is then filtered out. The washing process is repeated three times. Finally, the white precipitate is dried in a 60 degree vacuum oven to a moisture content of 20 ppm or less.

Synthesis Method of N-octyl-N-methylpyrrolidinium hexafluorophosphate (PYR$_{18}$PF$_6$)

The N-octyl-N-methylpyrrolidinium bromide synthesized in Step 1 is added to a molar amount (1M) of potassium hexafluorophosphate(KPF$_6$), followed by addition of deionized water. The ratio of deionized water to the bromine salt is 1:1 wt. %. The mixture is stirred at room temperature until reaction is completed. The white precipitate is filtered out and is placed in a container. Deionized water is added for washing and the white precipitate is then filtered out. The washing process is repeated three times. Finally, the white precipitate is dried in a 60 degree vacuum oven to a moisture content of 20 ppm or less.

Synthesis Method of N-nonyl-N-methylpyrrolidinium hexafluorophosphate (PYR$_{19}$PF$_6$)

The N-nonyl-N-methylpyrrolidinium bromide synthesized in Step 1 is added to a molar amount of potassium hexafluorophosphate(KPF$_6$), followed by addition of deionized water. The ratio of deionized water to the bromine salt is 1:1 wt. %. The mixture is stirred at room temperature until reaction is completed, and the resulting white precipitate is filtered out. The white precipitate is removed and placed in a container. Deionized water is added for washing and the white precipitate is then filtered out. The washing process is repeated three times. Finally, the precipitate is dried in a 60 degree vacuum oven to a moisture content of 20 ppm or less.

Synthesis Method of N-decyl-N-methylpyrrolidinium hexafluorophosphate (PYR$_{110}$PF$_6$)

The N-decyl-N-methylpyrrolidinium bromide synthesized in Step 1 is added to a molar amount of potassium hexafluorophosphate(KPF$_6$), followed by addition of deionized water. The ratio of deionized water to the bromine salt is 1:1 wt. %. The mixture is stirred at room temperature until reaction is completed, and the resulting white precipitate is filtered out. The white precipitate is removed and placed in a container. Deionized water is added for washing and the white precipitate is then filtered out. The washing process is repeated three times. Finally, the precipitate is dried in a 60 degree vacuum oven to a moisture content of 20 ppm or less.

Additives are introduced to the PYR$_{1R}$PF$_6$, series ionic liquid to enhance the battery life cycle as well as to counter any negative side effects. The followings are the method of synthesis of the useful additives.

Synthesis Method of N-butyl-N-methylpyrrolidinium bis(mandelato)borate (PYR$_{14}$BMB)

The N-butyl-N-methylpyrrolidinium bromide salt synthesized in Step 1 is added to a molar amount (1M) of NaBMB, followed by addition of deionized water. The ratio of deionized water to the bromine salt is 1:1 wt. %. The mixture is stirred at room temperature until reaction is completed. Dichloromethane is added to the mixture and the amount of dichloromethane added is the same as the amount of deionized water added to the bromine salt in the mixture. The Dichloromethane is separated and washed with a small amount of deionized water. The deionized water is then removed. The washing process is repeated for three times, followed by heating. The dichloromethane is removed by evaporation to obtain PYR$_{14}$BMB. The product is placed in a 60 degree vacuum oven until its moisture content is of 100 ppm or less.

Synthesis Method of N-butyl-N-methylpyrrolidinium bis(oxalate)borate (PYR$_{14}$BOB)

The N-butyl-N-methylpyrrolidinium bromide salt synthesized in Step 1 is added to an equimolar of NaBOB, followed by the addition of deionized water for mixing. The ratio of deionized water to the bromide salt is 1:1 wt. %. The mixture is stirred at room temperature until reaction is completed. Dichloromethane is added to the mixture and the amount of dichloromethane added is the same as the amount of deionized water added to the bromine salt in the mixture. The Dichloromethane is separated and washed with a small amount of deionized water. The deionized water is then removed. The washing process is repeated for three times, followed by heating. The dichloromethane is removed by evaporation to obtain $PYR_{14}BOB$. The product is placed in a 60 degree vacuum oven until its moisture content is of 100 ppm or less.

Synthesis Method of N-butyl-N-methylpyrrolidinium difluoro(oxalate)borate ($PYR_{14}ODFB$)

The N-butyl-N-methylpyrrolidinium bromide salt synthesized in Example 1 is added to an equimolar of NaODFB, followed by the addition of deionized water for mixing. The ratio of the deionized water to the bromide salt is 1:1 wt. %. The mixture is stirred at room temperature until the reaction is completed. Dichloromethane is added to the mixture and the amount of dichloromethane added is the same as the amount of deionized water added to the bromine salt in the mixture. The Dichloromethane is separated and washed with a small amount of deionized water. The deionized water is then removed. The washing process is repeated for three times, followed by heating. The dichloromethane is removed by evaporation to obtain $PYR_{14}ODFB$. The product is placed in a 60 degree vacuum oven until its moisture content is of 100 ppm or less.

Synthesis Method of N-butyl-N-methylpyrrolidinium bis(trifluoromethanesulfonyl)imide ($PYR_{14}TFSI$)

The N-butyl-N-methylpyrrolidinium bromide salt synthesized in Step 1 is added to the an equimolar of LiTFSI, followed by the addition of deionized water for mixing. The ratio of deionized water to the bromine salt is 1:1 wt. %. The mixture is stirred at room temperature until the reaction is completed. $PYR_{14}TFSI$ is not water soluble while LiBr is and therefore $PYR_{14}TFSI$ (organic matter) can easily be separated. The organic matter is washed with deionized water, and separated, and the washing process is repeated three times. Finally, the product was dried in a 60 degree vacuum oven until its moisture content is of 20 ppm or less.

Synthesis Method of N-butyl-N-methylpyrrolidinium bis(fluorosulfony)imide ($PYR_{14}FSI$)

The N-butyl-N-methylpyrrolidinium bromide salt synthesized in Step 1 is added to the equimolar LiFSI, followed by the addition of DI water, and the ratio of the DI water content to the bromide salt is 1:1 wt. %. After stirring at room temperature until the reaction is completed, the organic matter $PYR_{14}FSI$ (not water soluble) is separated from LiBr (water soluble), and $PYR_{14}FSI$ is washed with deionized water and separated, and the washing process is repeated three times. Finally, the product is dried in a 60 degree vacuum oven until its moisture content is of 20 ppm or less.

Figure 2:
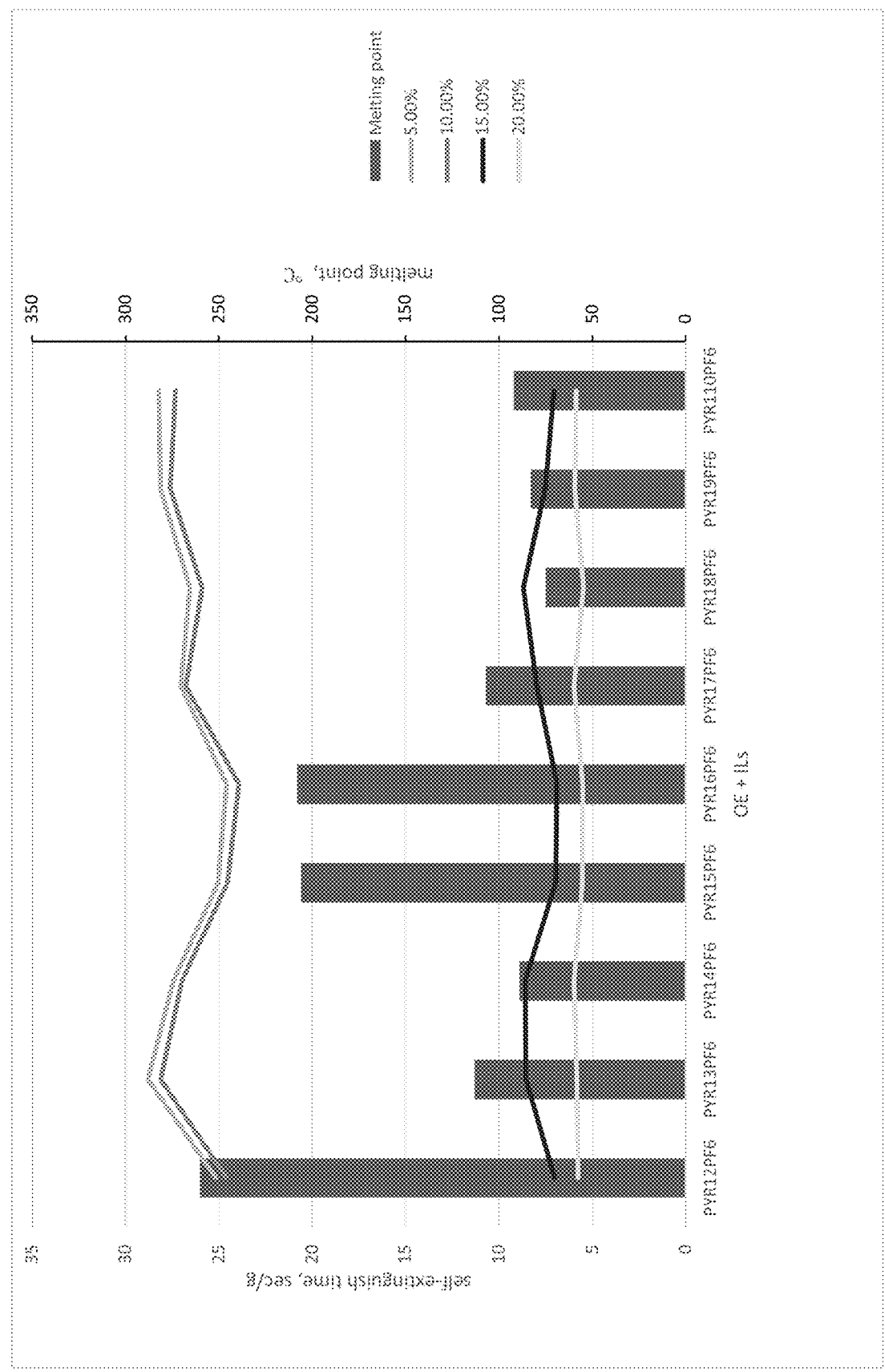
FIG. 2 is bar chart showing the self-extinguish time in second per gram and the melting point in degree Celsius of $PYR_{12}PF_6$, $PYR_{13}PF_6$, $PYR_{14}PF_6$, $PYR_{15}PF_6$, $PYR_{16}PF_6$, $PYR_{17}PF_6$, $PYR_{18}PF_6$, $PYR_{19}PF_6$, and $PYR_{110}PF_6$.

$PYR_{1R}PF_6$ with other carbon chains can be synthesized with the bromide salt in Step 1 in Step 2 synthesis method to produce the desired $PYR_{1R}PF_6$ series ionic liquid Self-Extinguish Test of $PYR_{1R}PF_6$, R=2~10 Series Ionic Liquids $PYR_{1R}PF_6$, R=2~10 series ionic liquids were synthesized and detected by differential scanning calorimetry (DSC) which shows that the series of ionic liquids are in solid state at room temperature. They are mixed with an organic solvent (a proton solvent) according to different ratios (5-20 wt. %) and tested for self-extinguish time (SET). With reference to FIG. 2, the amount of $PYR_{1R}PF_6$ is 5.00, 10.00, 15.00 and 20.00 wt. %.

In FIG. 2, the self-extinguishing test is performed by dropping a 1.2 g of the electrolyte on a 47 mm diameter glass fiber membrane with a thickness of 0.5 mm.

Ignition timing test is then performed.

$PYR_{12}PF_6$ has a melting point of 260 degree Celsius. 5 wt % of $PYR_{12}PF_6$ has a self-extinguish time of about 25.1 seconds per gram. 10 wt % of $PYR_{12}PF_6$ has a self-extinguish time of about 24.6 seconds per gram. 15 wt % of $PYR_{12}PF_6$ has a self-extinguish time of about 7 seconds per gram. 20 wt % of $PYR_{12}PF_6$ has a self-extinguish time of about 6 seconds per gram.

$PYR_{13}PF_6$ has a melting point of 113 degree Celsius. 5 wt % of $PYR_{13}PF_6$ has a self-extinguish time of about 28.8 seconds per gram. 10 wt % of $PYR_{13}PF_6$ has a self-extinguish time of about 28.1 seconds per gram. 15 wt % of $PYR_{13}PF_6$ has a self-extinguish time of about 8.6 seconds per gram. 20 wt % of $PYR_{13}PF_6$ has a self-extinguish time of about 6 seconds per gram.

$PYR_{14}PF_6$ has a melting point of 89 degree Celsius. 5 wt % of $PYR_{14}PF_6$ has a self-extinguish time of about 27.4 seconds per gram. 10 wt % of $PYR_{14}PF_6$ has a self-extinguish time of about 27 seconds per gram. 15 wt % of $PYR_{14}PF_6$ has a self-extinguish time of about 8.6 seconds per gram. 20 wt % of $PYR_{14}PF_6$ has a self-extinguish time of about 6 seconds per gram.

$PYR_{15}PF_6$ has a melting point of 206 degree Celsius. 5 wt % of $PYR_{15}PF_6$ has a self-extinguish time of about 25 seconds per gram. 10 wt % of $PYR_{15}PF_6$ has a self-extinguish time of about 24.5 seconds per gram. 15 wt % of $PYR_{15}PF_6$ has a self-extinguish time of about 7 seconds per gram. 20 wt % of $PYR_{15}PF_6$ has a self-extinguish time of about 6 seconds per gram.

$PYR_{16}PF_6$ has a melting point of 208 degree Celsius. 5 wt % of $PYR_{16}PF_6$ has a self-extinguish time of about 24.5 seconds per gram. 10 wt % of $PYR_{16}PF_6$ has a self-extinguish time of about 23.9 seconds per gram. 15 wt % of $PYR_{16}PF_6$ has a self-extinguish time of about 7 seconds per gram. 20 wt % of $PYR_{16}PF_6$ has a self-extinguish time of about 6 seconds per gram.

$PYR_{17}PF_6$ has a melting point of 107 degree Celsius. 5 wt % of $PYR_{17}PF_6$ has a self-extinguish time of about 27 seconds per gram. 10 wt % of $PYR_{17}PF_6$ has a self-extinguish time of about 26.8 seconds per gram. 15 wt % of $PYR_{17}PF_6$ has a self-extinguish time of about 8 seconds per gram. 20 wt % of $PYR_{17}PF_6$ has a self-extinguish time of about 6 seconds per gram.

$PYR_{18}PF_6$ has a melting point of 75 degree Celsius. 5 wt % of $PYR_{18}PF_6$ has a self-extinguish time of about 26.5 seconds per gram. 10 wt % of $PYR_{18}PF_6$ has a self-extinguish time of about 25.9 seconds per gram. 15 wt % of $PYR_{18}PF_6$ has a self-extinguish time of about 8.7 seconds per gram. 20 wt % of $PYR_{18}PF_6$ has a self-extinguish time of about 6 seconds per gram.

$PYR_{19}PF_6$ has a melting point of 83 degree Celsius. 5 wt % of $PYR_{19}PF_6$ has a self-extinguish time of about 28.1 seconds per gram. 10 wt % of $PYR_{19}PF_6$ has a self-extinguish time of about 27.6 seconds per gram. 15 wt % of $PYR_{19}PF_6$ has a self-extinguish time of about 7.5 seconds per gram. 20 wt % of $PYR_{19}PF_6$ has a self-extinguish time of about 6 seconds per gram.

$PYR_{110}PF_6$ has a melting point of 92 degree Celsius. 5 wt % of $PYR_{110}PF_6$ has a self-extinguish time of about 28.2 seconds per gram. 10 wt % of $PYR_{110}PF_6$ has a self-extinguish time of about 27.3 seconds per gram. 15 wt % of $PYR_{110}PF_6$ has a self-extinguish time of about 7.1 seconds per gram. 20 wt % of $PYR_{110}PF_6$ has a self-extinguish time of about 6 seconds per gram.

As shown in FIG. 2, the addition of $PYR_{1R}PF_6$, R=2~10, up to 15 wt % have good self-extinguishing properties which is in general below 9 seconds per gram.

When the added amount of $PYR_{1R}PF_6$, R=2~10 reaches 20 wt %, the self-extinguishing time reaches about 6 sec/g. When the added amount reaches 40 wt %, the self-extinguishing time reaches 5 sec/g.

At lower concentration, 5 wt %, 10 wt %, 15 wt % of $PYR_{1R}PF_6$, R=2~10, the self-extinguishing times of $PYR_{1R}PF_6$, R=2-10, with melting point higher than 200 degree Celsius are better than the self-extinguishing times of $PYR_{1R}PF_6$, R=2-10, with melting point lower than 200 degree Celsius.

$PYR_{1R}PF_6$ series ionic liquids is commercially attractive given that the synthesis is relatively straight forward and hence the costs for doing so is relatively low.

Battery Performance Test of Battery with $PYR_{1R}PF_6$, R=2~10 as the Ionic Liquid Flame Retardant in the Electrolyte Charge and discharge battery performance test is conducted on the battery with $PYR_{1R}PF_6$, R=2~10 as the ionic liquid flame retardant using the Neware Battery Performance Test System. Side reaction test is also performed using Autolab 302N Electrochemical Workstation.

$PYR_{1R}PF_6$, R=2~10 ionic liquid flame retardant is mixed with an organic electrolyte (OE) comprises 1M $LiPF_6$ with ethylene carbonate(EC)/dimethyl carbonate(DMC)/diethyl carbonate(DEC) at 1:1:1 vol % and 3.5 wt % vinylene carbonate (VC). The overall amounts of $PYR_{1R}PF_6$, R=2~10 and OE in the batteries being tested are detailed in FIG. 3. The battery performance test was conducted with the Neware Battery Performance Test System and any side reaction test was tested with the Autolab 302N Electrochemical Workstation.

In both the battery performance test, the battery contains a positive electrode, a negative electrode, a separator and an electrolyte.

Positive electrode is a composition of the electrode is 90 wt % $LiFePO_4$+5 wt % Super P+5 wt % PVDF.

Negative A electrode is a composition of the electrode is MCMB 92 wt %+Super P 5 wt %+3 wt % PVDF.

Separator is a ceramic coated polypropylene separator with a thickness of 20 um.

Electrolyte is a mixture of organic electrolyte and ionic liquid, the organic electrolyte being 1M $LiPF_6$ with ethylene carbonate (EC)/dimethyl carbonate (DMC)/diethyl carbonate (DEC)(1:1:1 vol %)+3.5 wt % vinylene carbonate (VC) with different ratios of $PYR_{1R}PF_6$ for charge and discharge tests.

Charge and discharge conditions: 0.2 C-rate is charged and discharged.

Cut-off condition: The battery is judged to be invalid when the cycle charge/discharge capacity drops below 80% of the original capacity.

In the side reaction test, also known as the side reaction peak test, is performed using three-electrode test method.

Working electrode comprises Negative A which is MCMB 92 wt %+Super P 5 wt %+3 wt % PVDF.

Reference electrode comprises lithium metal

Counter electrode comprises lithium metal

Scan range of the test is 0-2.5V and the scan rate is 1 mV/s

As summarized in FIG. 3, side reaction is inevitable when the flame retardant $PYR_{1R}PF_6$, R=2~10, is added. The addition of any one of $PYR_{12}PF_6$. $PYR_{13}PF_6$, $PYR_{14}PF_6$, $PYR_{15}PF_6$, $PYR_{16}PF_6$, $PYR_{17}PF_6$, $PYR_{18}PF_6$, $PYR_{19}PF_6$ and $PYR_{110}PF_6$ shows side reaction in the tested sample, irrespective of the overall amount of OE and IL mixture i.e. 5 wt % (of electrolyte), 10 wt % (of electrolyte), 15 wt % (of electrolyte) and 20 wt % (of electrolyte). Furthermore, The addition of $PYR_{1R}PF_6$, R=2~10, has substantial negative impact on the cycle life of the battery, resulting in no more than 100 charge and discharge cycles before the charge and discharge capacity drops below 80% of the original capacity. The value is too low to have commercial value. Worth noting, there is a general trend in which the larger the amount of $PYR_{12}PF_6$, $PYR_{11}PF_6$, $PYR_{14}PF_6$, $PYR_{15}PF_6$, $PYR_{16}PF_6$, $PYR_{17}PF_6$, $PYR_{18}PF_6$, $PYR_{19}PF_6$ and $PYR_{110}PF_6$, the lower the number of charge and discharge cycles before the charge and discharge capacity drops below 80% of the original capacity.

Figure 4:
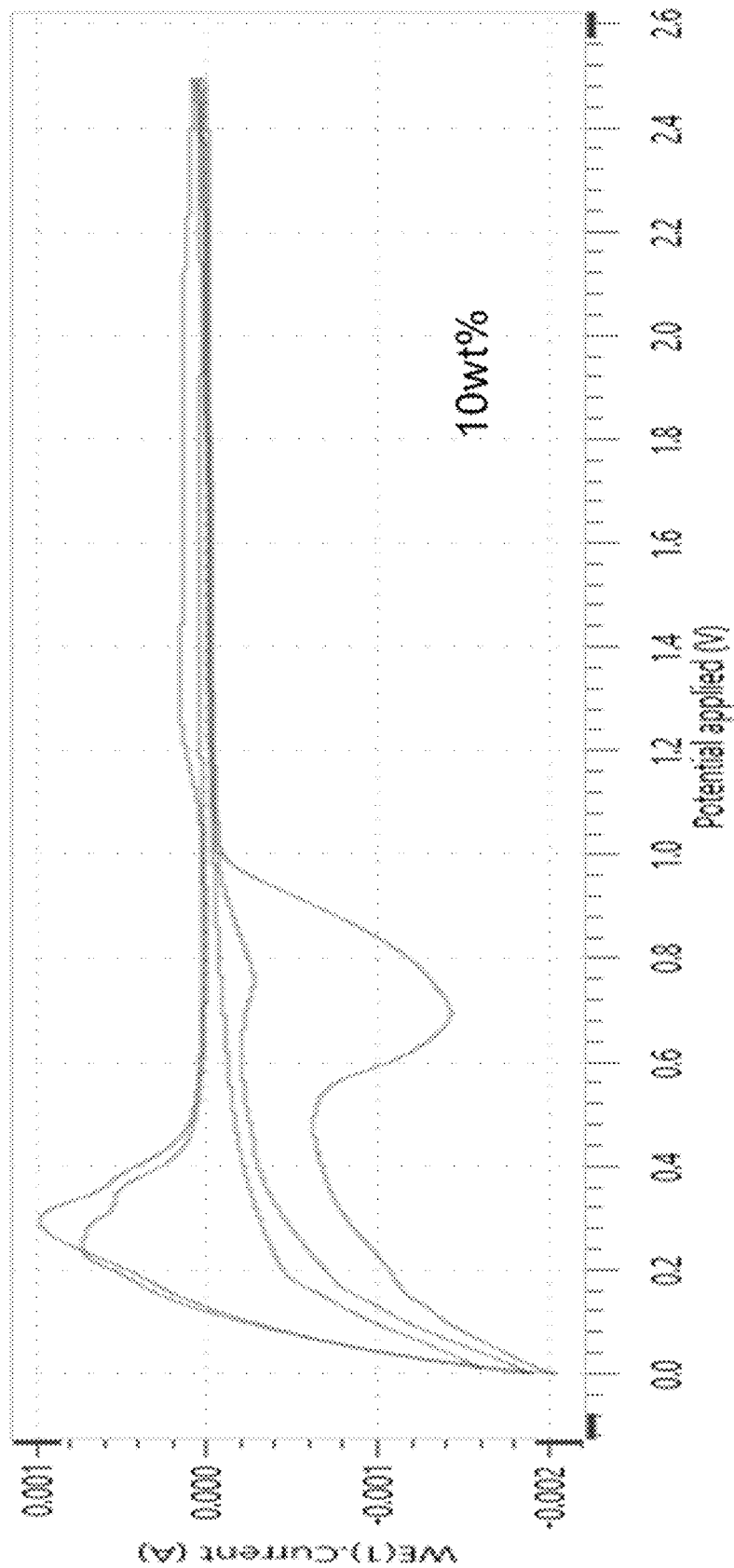
FIG. 4 is a cyclic voltammetry line graph showing the side reaction measurable at 0.5V to 1.0V of the battery with electrolyte comprises 90 wt % of 1M $LiPF_6$ with ethylene carbonate (EC)/dimethyl carbonate (DMC)/diethyl carbonate (DEC)(1:1:1 vol %)+3.5 wt % vinylene carbonate (VC) and 10 wt. % $PYR_{16}PF_6$.
Figure 5:
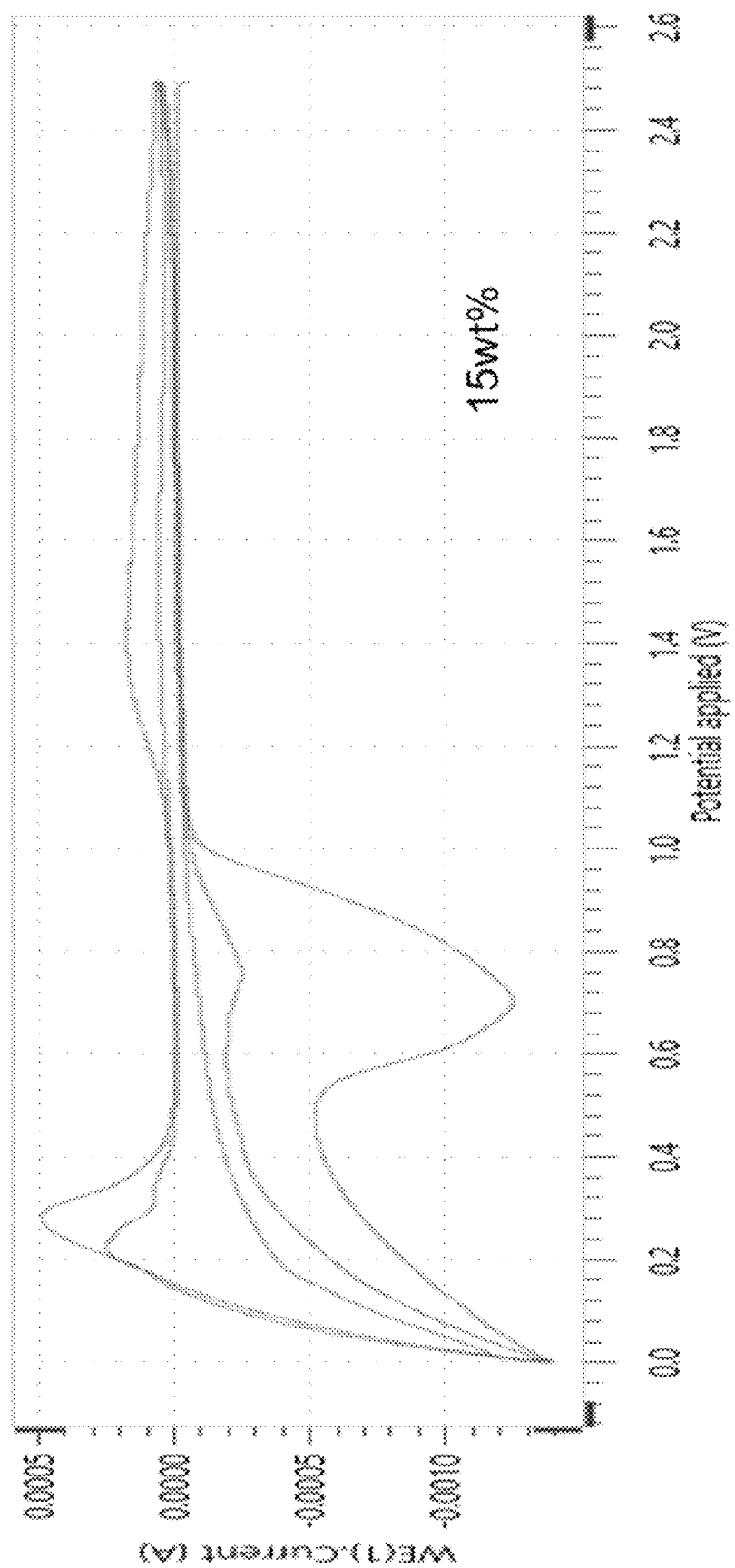
FIG. 5 is a cyclic voltammetry line graph showing the side reaction measurable at 0.5V to 1.0V of the battery with electrolyte comprises 85 wt % of 1M $LiPF_6$ with ethylene carbonate (EC)/dimethyl carbonate (DMC)/diethyl carbonate (DEC)(1:1:1 vol %)+3.5 wt % vinylene carbonate (VC) and 15 wt. % $PYR_{16}PF_6$.
Figure 6:
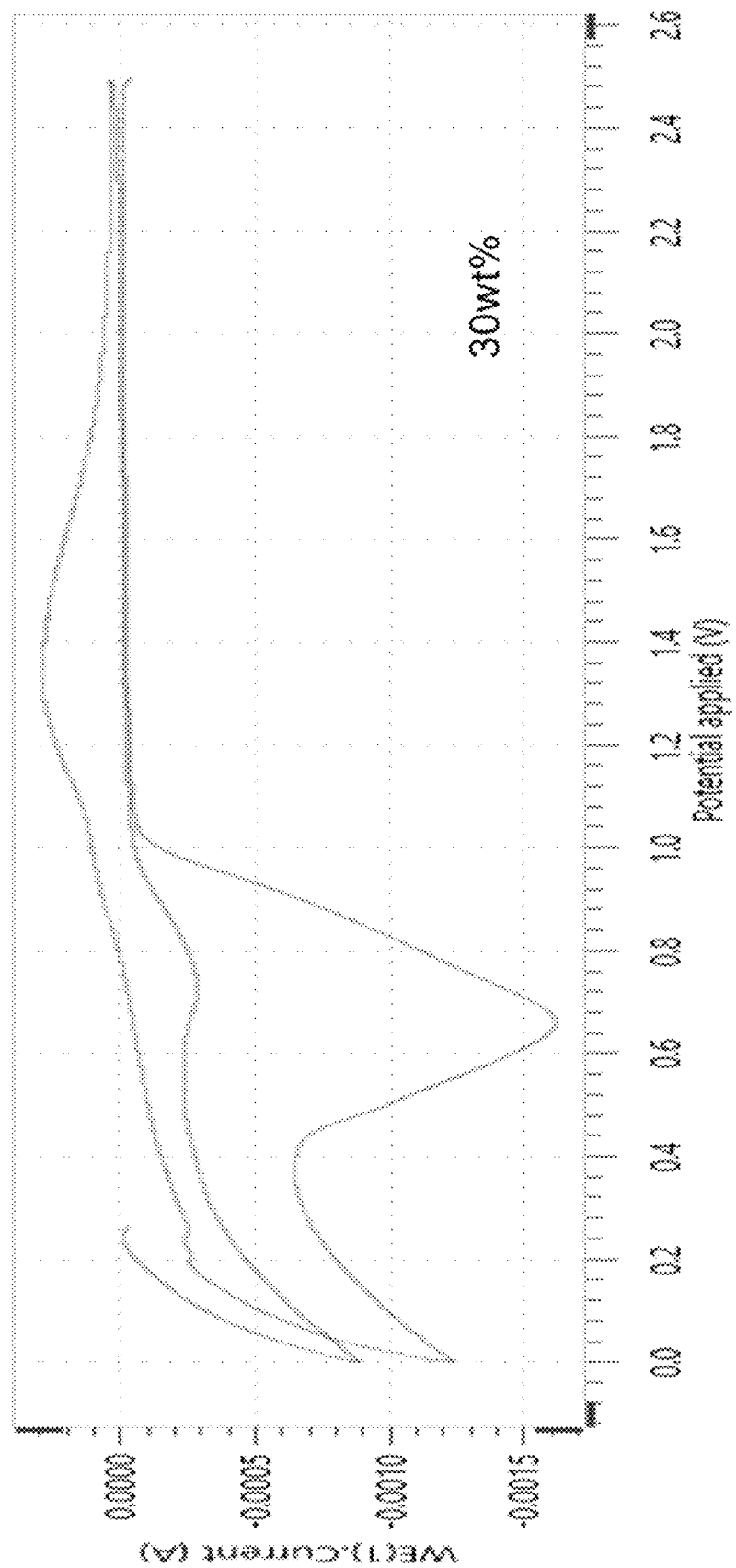
FIG. 6 is a cyclic voltammetry line graph showing the side reaction measurable at 0.4V to 1.0V of the battery with electrolyte comprises 70 wt % of 1M $LiPF_6$ with ethylene carbonate (EC)/dimethyl carbonate (DMC)/diethyl carbonate (DEC)(1:1:1 vol %)+3.5 wt % vinylene carbonate (VC) and 30 wt. % $PYR_{16}PF_6$.

Referring to FIGS. 4 to 6 which show the cyclic voltammetry of the battery with electrolyte having different amounts of $PYR_{1R}PF_6$ where R=6. The cyclic voltammetries indicate that the side reactions peak between 0.4~1 V. It can also be concluded that there is a direction relationship between the amount of $PYR_{16}PF_6$ and the intensity of the side reaction peak. In general, the more the amount of $PYR_{1R}PF_6$ where R=6, the more obvious (higher intensity) the side reaction peak.

In FIG. 4, there is shown a cyclic voltammetry graph of a battery. Electrolyte of the battery includes 10 wt. % of $PYR_{16}PF_6$. The side reaction peak is shown at 0.5-1V with an intensity of −0.0014 A.

In FIG. 5, there is shown a cyclic voltammetry graph of a battery.

Electrolyte of the battery includes 15 wt. % of $PYR_{16}PF_6$. The side reaction peak is shown at 0.5-1V with an intensity of −0.0015 A.

In FIG. 6, there is shown a cyclic voltammetry graph of a battery. Electrolyte of the battery includes 30 wt. % of $PYR_{16}PF_6$. The side reaction peak is shown at 0.5-1V with an intensity of −0.0016 A.

Ionic Liquid Flame Retardant with Melting Point Above 200 Degree Celsius

The following tests aim at showing although charging and discharging are possible or can be performed, the side reaction eventually lead to decrease in charging and discharging of battery cycle. The side reaction affects the life cycle of a battery. The side reaction can be a result of reduction and deposition reaction of $PYR_{1R}PF_6$ and the pre-intercalation of $PY_{1R}PF_6$. Both affects the intercalation and deintercalation of Lithium ion.

$PYR_{1R}PF_6$ where R=2, 5, 6 have melting points above 200 degree Celsius. Batteries formed from electrolyte having different amounts of $PYR_{1R}PF_6$, $PYR_{15}PF_6$, or $PYR_{16}PF_6$ mixed with organic electrolyte(OE) comprises 1M $LiPF_6$ with ethylene carbonate (EC)/dimethyl carbonate (DMC)/diethyl carbonate (DEC)(1:1:1 vol %)+3.5 wt % vinylene carbonate (VC) are tested. With reference to FIG. 7, details of the composition of the electrolytes in each of the tested batteries (Samples 1 to 11) are discussed below. The results of the tests are shown in FIG. 7 and it is indicated that the battery charge and discharge cycle life performance is poor with the presence of $PYR_{12}PF_6$, $PYR_{15}PF_6$, or $PYR_{16}PF_6$.

The Samples 1 to 11 and a control Sample A are tested with the Neware Battery Performance Test System. In the test system, the battery contains a positive electrode, a negative electrode, a separator and an electrolyte Positive electrode comprises a composition of the electrode is 90 wt % $LiFePO_4$+5 wt % Super P+5 wt % PVDF Negative A electrode comprises a composition of the electrode is MCMB 92 wt %+Super P 5 wt %+3 wt % PVDF.

Negative B electrode comprises a composition of the electrode is MCMB 80 wt %+Super P 4 wt %°+1 wt % VGCF+10 wt % SiOx/C+5 wt % SBR A separator comprises ceramic coated polypropylene separator with a thickness of 20 um.

Charge and discharge at 0.2 C-rate.

Cut-off condition: The battery is considered invalid when the charge and discharge cycle capacity drops below 80% of the original capacity.

Electrolyte: Sample 1 to 11—Different amount of $PYR_{12}PF_6$, $PYR_{15}PF_6$, or $PYR_{16}PF_6$ mixed with organic solvent (OE) comprises 1M $LiPF_6$ with ethylene carbonate (EC)/dimethyl carbonate (DMC)/diethyl carbonate (DEC) (1:1:1 vol %)+3.5 wt % vinylene carbonate (VC). Sample A-OE alone.

In the Sample A, the electrolyte contains 100% of organic electrolyte (OE), which is without any $PYR_{1R}PF_6$. The number of charge and discharge life cycle of Negative A electrode is 2163 and that of Negative B electrode is 513.

In the Sample 1, 5 wt % of $PYR_{12}PF_6$ is added to 95 wt % of OE. The number of charge and discharge life cycle of Negative A electrode is 98 and that of Negative B electrode is 105.

In Sample 2, 5 wt % of $PYR_{15}PF_6$ is added to 95 wt % of OE. The number of charge and discharge life cycle of Negative A electrode is 94 and that of Negative B electrode is 104.

In Sample 3, 5 wt % of $PYR_{16}PF_6$ is added to 95 wt % of OE. The number of charge and discharge life cycle of Negative A electrode is 97 and that of Negative B electrode is 102.

In Sample 4, 0 wt % of $PYR_{12}PF_6$ is added to 90 wt % of OE. The number of charge and discharge life cycle of Negative A electrode is 63 and that of Negative B electrode is 78.

In Sample 5, 10 wt % of $PYR_{15}PF_6$ is added to 90 wt % of OE. The number of charge and discharge life cycle of Negative A electrode is 50 and that of Negative B electrode is 69.

In Sample 6, 10 wt % of $PYR_{16}PF_6$ is added to 90 wt % of OE. The number of charge and discharge life cycle of Negative A electrode is 56 and that of Negative B electrode is 72.

In Sample 7, 20 wt % of $PYR_{12}PF_6$ is added to 80 wt % of OE. The number of charge and discharge life cycle of Negative A electrode is 38 and that of Negative B electrode is 37.

In Sample 8, 20 wt % of $PYR_{15}PF_6$ is added to 80 wt % of OE. The number of charge and discharge life cycle of Negative A electrode is 40 and that of Negative B electrode is 40.

In Sample 9, 20 wt % of $PYR_{16}PF_6$ is added to 80 wt % of OE. The number of charge and discharge life cycle of Negative A electrode is 32 and that of Negative B electrode is 32.

In Sample 10, $PYR_{12}PF_6$: $PYR_{15}PF_6$: $PYR_{16}PF_6$:OE in the ratio of 10 wt %:5 wt %:5 wt %:80 wt % is mixed. The number of charge and discharge life cycle of Negative A electrode is 36 and that of Negative B electrode is 36.

In Sample 11, $PYR_{16}PF_6$: $PYR_{15}PF_6$: $PYR_{16}PF_6$:OE in the ratio of 5 wt %:10%:5 wt %:80 wt % is mixed. The number of charge and discharge life cycle of Negative A electrode is 34 and that of Negative B electrode is 34.

Based on the above findings, in general, the higher the wt % of $PYR_{12}PF_6$, $PYR_{15}PF_6$, or $PYR_{16}PF_6$ in the electrolyte, the shorter the battery charge and discharge life cycle. By comparing with Sample A, Samples 1 to 11 have significantly lower number of cycle life in both Negative A and Negative B electrodes it is therefore concluded that the addition of $PYR_{12}PF_6$, $PYR_{15}PF_6$, or $PYR_{16}PF_6$ or even $PYR_{1R}PF_6$, where R=2 to 10 in to the electrolyte renders the battery not commercializable by shortening the life cycle of the battery significantly.

Battery Performance Tests Performed on Batteries with Electrolytes that Contains at Least One $PYR_{1R}$ Boron-Based Stabilizer In each of the tested batteries (Samples 1 to 15), the electrolyte comprise a mixture of an organic electrolyte (OE) comprises 1M $LiPF_6$ with ethylene carbonate (EC)/dimethyl carbonate (DMC)/diethyl carbonate (DECX1:1:1 vol %)+3.5 wt % vinylene carbonate (VC) and one of $PYR_{12}PF_6$, $PYR_{15}PF_6$, and $PYR_{16}PF_6$ which have melting points of above 200 degree Celsius. At least one $PYR_{1R}$ boron-based stabilizer is added to the electrolyte to improve or lengthen the life cycle of the batteries.

The specific amount of the first stabilizer in each of the Samples 1 to 15 batteries is provided in FIG. 8. The battery is tested with the Neware Battery Performance Test System and the cycle life of Negative A and Negative B electrodes are provided in FIG. 8. Sample 16 is a control with 100% OE and is also tested with the Neware Battery Performance Test System The presence of a $PYR_{1R}$ boron-based stabilizer (first stabilizer) improves or lengthens the cycle life of each of the batteries in Samples 1 to 15.

Battery Performance Test:

The battery contains a positive electrode, a negative electrode, a separator and an electrolyte.

Positive electrode comprises a composition of the electrode is 90 wt % $LiFePO_4$+5 w t % Super P+5 wt % PVDF.

Negative A electrode comprises a composition of the electrode is MCMB 92 wt %+Super P 5 wt %+3 wt % PVDF.

Negative B electrode comprises a composition of the electrode is MCMB 80 wt %+Super P 4 wt %+1 wt % VGCF+10 wt % SiOx/C+5 wt % SBR.

Separator comprises a ceramic coated polypropylene separator with a thickness of 20 um.

Electrolyte: Organic electrolyte (OE) comprises 1M $LiPF_6$ with ethylene carbonate (EC)/dimethyl carbonate (DMC)/diethyl carbonate (DECX)(1:1:1 vol %)+3.5 wt % vinylene carbonate (VC), one of $PYR_{12}PF_6$, $PYR_{15}PF_6$, and $PYR_{16}PF_6$ and a first stabilizer which is a $PYR_{1R}$ boron-based ionic liquid. The specific amount in wt. % of these constituents are provided in FIG. 8.

The battery is charged and discharged.

Charge and discharge at 0.2 C-rate.

The cut-off condition is when the battery is considered to be invalid i.e. when the charge and discharge cycle capacity drops below 80% of the original capacity.

Referring to FIG. 8:

In Sample 1, the OE:$PYR_{12}PF_6$:$PYR_{12}BOB$ ratio is 80 wt %:15 wt %:5 wt %. The number of charge and discharge life cycle of Negative A electrode in the resulting battery is 572 and that of Negative B electrode is 178.

In Sample 2, the OE:$PYR_{12}PF_6$:$PYR_{14}ODFB$ ratio is 80 wt %:15 wt %:5 wt %. The number of charge and discharge life cycle of Negative A electrode in the resulting battery is 558 and that of Negative B electrode is 182.

In Sample 3, the OE. $PYR_{12}PF_6PYR_{14}BMB$ ratio is 80 wt %:15 wt %:5 wt %. The number of charge and discharge life cycle of Negative A electrode in the resulting battery is 542 and that of Negative B electrode is 175.

In Sample 4, the OE:$PYR_{15}PF_6$:$PYR_{14}BOB$ ratio is 80 wt %:15 wt %:5 wt %. The number of charge and discharge life cycle of Negative A electrode in the resulting battery is 546 and that of Negative B electrode is 163.

In Sample 5, the OE:$PYR_{15}PF_6$:$PYR_{14}ODFB$ ratio is 80 wt %:15 wt %:5 wt % The number of charge and discharge life cycle of Negative A electrode in the resulting battery is 537 and that of Negative B electrode is 149.

In Sample 6, the OE:$PYR_{15}PF_6$:$PYR_{14}BMB$ ratio is 80 wt %:15 wt %:5 wt %. The number of charge and discharge life cycle of Negative A electrode in the resulting battery is 523 and that of Negative B electrode is 152.

In Sample 7, the OE:$PYR_{16}PF_6$:$PYR_{14}BOB$ ratio is 80 wt %:15 wt %:5 wt %. The number of charge and discharge life cycle of Negative A electrode in the resulting battery is 539 and that of Negative B electrode is 184.

In Sample 8, the OE. $PYR_{16}PF_6$:$PYR_{14}ODFB$ ratio is 80 wt %:15 wt %:5 wt %. The number of charge and discharge life cycle of Negative A electrode in the resulting battery is 542 and that of Negative B electrode is 172.

In Sample 9, the OE:$PYR_{16}PF_6$:$PYR_{14}BMB$ ratio is 80 wt %:15 wt %:5 wt %.

The number of charge and discharge life cycle of Negative A electrode in the resulting battery is 512 and that of Negative B electrode is 167.

In Sample 10, the OE:$PYR_{15}PF_6$:$PYR_{14}BOB$ ratio is 87 wt %:10 wt %:3 wt %. The number of charge and discharge life cycle of Negative A electrode in the resulting battery is 785 and that of Negative B electrode is 198.

In Sample 11, the OE:$PYR_{15}PF_6$:$PYR_{14}ODFB$ ratio is 87 wt %:10 wt %:3 wt %. The number of charge and discharge life cycle of Negative A electrode in the resulting battery is 769 and that of Negative B electrode is 221.

In Sample 12, the OE:$PYR_{15}PF_6$:$PYR_{14}BMB$ ratio is 87 wt %:10 wt %:3 wt %. The number of charge and discharge life cycle of Negative A electrode in the resulting battery is 743 and that of Negative B electrode is 203.

In Sample 13, the OE. $PYR_{12}PF_6$:$PYR_{14}BOB$ ratio is 94 wt %:5 wt %:1 wt %. The number of charge and discharge life cycle of Negative A electrode in the resulting battery is 925 and that of Negative B electrode is 234.

In Sample 14, the OE:$PYR_{12}PF_6$:$PYR_{14}ODFB$ ratio is 94 wt %:5 wt %:1 wt %. The number of charge and discharge life cycle of Negative A electrode in the resulting battery is 937 and that of Negative B electrode is 252.

In Sample 15, the OE:$PYR_{12}PF_6$:$PYR_{14}BMB$ ratio is 94 wt %:5 wt %:1 wt %. The number of charge and discharge life cycle of Negative A electrode in the resulting battery is 909 and that of Negative B electrode is 226.

In Sample 16, which is a control, the electrolyte comprises only 100 wt % OE. The number of charge and discharge life cycle of Negative A electrode in the resulting battery is 2163 and that of Negative B electrode is 513.

The results show that the cycle life of a battery with electrolyte formed from a mixture of OE and one of $PYR_{12}PF_6$, $PYR_{15}PF_6$, and $PYR_{16}PF_6$ is noticeably improved by the addition of a $PYR_{1R}$ boron-based first stabilizer.

Battery performance tests performed on batteries with electrolytes that contain a first and a second stabilizer. It is concluded that similar result will be shown in batteries with electrolyte mixture of OE, $PYR_{1R}PF_6$ where R=2 to 10 and a first stabilizer ($PYR_{1R}$ boron-based).

Battery Performance Test System.

The battery contains a positive electrode, a negative electrode, a separator and an electrolyte.

The Positive electrode comprises a composition of 90 wt % $LiFePO_4$+5 wt % Super P+5 wt % PVDF.

The Negative A electrode comprises a composition of MCMB 92 wt %+Super P 5 wt %+3 wt % PVDF.

The Negative B electrode comprises a composition of MCMB 80 wt %+Super P 4 wt %+1 wt % VGCF+10 wt % SiOx/C+5 wt % SBR.

The separator comprises a ceramic coated polypropylene separator with a thickness of 20 um.

The electrolytes at the negative electrode A and the negative electrode B are different. They both comprise $PYR_{15}PF_6$, a first $PYR_{1R}$ boron-based stabilizer, $PYR_{14}BOB$, $PYR_{14}ODFB$ or $PYR_{14}BMB$ and a second stabilizer which is preferably $PYR_{1R}$-TFSI or $PYR_{1R}$-FSI.

The OE at negative electrode A is 1M $LiPF_6$ with ethylene carbonate (EC)/dimethyl carbonate (DMC)/diethyl carbonate (DECX1:1:1 vol %)+3.5 wt % vinylene carbonate (VC).

The OE at negative electrode B is 1M $LiPF_6$ with ethylene carbonate (EC)/dimethyl carbonate (DMC)/diethyl carbonate (DECX1:1:1 vol %)+3.5 wt % fluoroethylene carbonate (FEC).

Details of the amount of various constituents in the electrolyte of the batteries (Samples 1 to 21) are provided in FIG. 9.

The resulting batteries are tested with the Neware Battery Performance Test System, being charged and discharged at 0.2 C-rate.

The Cut-off condition: The battery is considered to be invalid when the charge and discharge cycle capacity drops below 80% of the original capacity.

Based on the findings in FIG. 9, it is concluded that the addition of a second stabilizer ($PYR_{14}FSI$ or $PYR_{14}TFSI\_$ to an electrolyte mixture of OE, $PYR_{15}PF_6$ and first stabilizer ($PYR_{14}BOB$ or $PYR_{14}ODFB$) in a battery further improves the cycle life of that battery when compared to the battery with only a first stabilizer as an additive to the electrolyte.

With reference to FIG. 9:

In Sample 1, the electrolyte comprises OE, $PYR_{15}PF_6$, $PYR_{14}BOB$, and $PYR_{14}TFSI$. The OE:$PYR_{15}PF_6$:$PYR_{14}BOB$:$PYR_{14}TFSI$ ratio is 79 wt %:15 wt %:5 wt %:1 wt % The number of charge and discharge life cycle of Negative A electrode in the resulting battery is 789 and that of Negative B electrode is 210.

In Sample 2, the electrolyte comprises OE, $PYR_{15}PF_6$, $PYR_{14}ODFB$, and $PYR_{14}TFSI$. The OE:$PYR_{15}PF_6$:$PYR_{14}ODFB$:$PYR_{14}TFSI$ ratio is 79 wt %:15 wt %:5 wt %:1 wt %. The number of charge and discharge life cycle of Negative A electrode in the resulting battery is 801 and that of Negative B electrode is 201.

In Sample 3, the electrolyte comprises OE, $PYR_{15}PF_6$, $PYR_{14}BOB$ and $PYR_{14}FSI$ the OE:$PYR_{15}PF_6$:$PYR_{14}BOB$:$PYR_{14}FSI$ ratio is 79 wt %:15 wt %:5 wt %:1 wt %. The number of charge and discharge life cycle of Negative A electrode in the resulting battery is 537 and that of Negative B electrode is 215.

In Sample 4, the electrolyte comprises OE, $PYR_{15}PF_6$, $PYR_{14}ODFB$ and $PYR_{14}FSI$. The $OE:PYR_{15}PF_6$: $PYR_{14}ODFB:PYR_{14}FSI$ ratio is 79 wt %:15 wt %:5 wt %:1 wt % The number of charge and discharge life cycle of Negative A electrode in the resulting battery is 521 and that of Negative B electrode is 228.

In Sample 5, the electrolyte comprises OE, $PYR_{15}PF_6$, $PYR_{14}BOB$ and $PYR_{14}TFSI$. The $OE:PYR_{15}PF_6$: $PYR_{14}BOB:PYR_{14}TFSI$ ratio is 84 wt %:10 wt %:5 wt:1 wt %. The number of charge and discharge life cycle of Negative A electrode in the resulting battery is 1321 and that of Negative B electrode is 241.

In Sample 6, the electrolyte comprises OE, $PYR_{15}PF_6$, $PYR_{14}ODFB$ and $PYR_{14}TFSI$. The $OE:PYR_{15}PF_6$: $PYR_{14}ODFB:PYR_{14}TFSI$ ratio is 84 wt %:10 wt %:5 wt %:1 wt %. The number of charge and discharge life cycle of Negative A electrode in the resulting battery is 1318 and that of Negative B electrode is 238.

In Sample 7, the electrolyte comprises OE, $PYR_{15}PF_6$, $PYR_{14}BOB$ and $PYR_{14}FSI$. The $OE:PYR_{15}PF_6$: $PYR_{14}BOB:PYR_{14}FSI$ ratio is 84 wt %:10 wt %:5 wt %:1 wt % The number of charge and discharge life cycle of Negative A electrode in the resulting battery is 759 and that of Negative B electrode is 253.

In Sample 8, the electrolyte comprises OE, $PYR_{15}PF_6$, $PYR_{14}ODFB$ and $PYR_{14}FSI$. The $OE:PYR_{15}PF_6$: $PYR_{14}ODFB:PYR_{14}FSI$ ratio is 84 wt %:15 wt %:5 wt %:1 wt %. The number of charge and discharge life cycle of Negative A electrode in the resulting battery is 773 and that of Negative B electrode is 257.

In Sample 9, the electrolyte comprises OE, $PYR_{15}PF_6$, $PYR_{14}BOB$ and $PYR_{14}TFSI$. The $OE:PYR_{15}PF_6$: $PYR_{14}BOB:PYR_{14}TFSI$ ratio is 82 wt %:10 wt %:5 wt %:3 wt %. The number of charge and discharge life cycle of Negative A electrode in the resulting battery is 1433 and that of Negative B electrode is 253.

In Sample 10, the electrolyte comprises OE. $PYRI PF_6$, $PYR_{14}ODFB$ and $PYR_{14}TFSI$. The $OE:PYR_{15}PF_6$: $PYR_{14}ODFB:PYR_{14}TFSI$ ratio is 82 wt %:10 wt %:5 wt %:3 wt %. The number of charge and discharge life cycle of Negative A electrode in the resulting battery is 1437 and that of Negative B electrode is 240.

In Sample 11, the electrolyte comprises OE, $PYR_{15}PF_6$, $PYR_{14}BOB$ and $PYR_{14}FSI$. The $OE:PYR_{15}PF_6$: $PYR_{14}BOB:PYR_{14}FSI$ ratio is 82 wt %:10 wt %:5 wt %:3 wt %. The number of charge and discharge life cycle of Negative A electrode in the resulting battery is 785 and that of Negative B electrode is 262.

In Sample 12, the electrolyte comprises OE, $PYR_{15}PF_6$, $PYR_{14}ODFB$ and $PYR_{14}FSI$ The $OE:PYR_{15}PF_6$: $PYR_{14}ODFB:PYR_{14}FSI$ ratio is 82 wt %:10 wt %:5 wt %:3 wt %. The number of charge and discharge life cycle of Negative A electrode in the resulting battery is 792 and that of Negative B electrode is 279.

In Sample 13, the electrolyte comprises OE. $PYR_{15}PF_6$, $PYR_{14}BOB$ and $PYR_{14}TFSI$. The $OE:PYR_{15}PF_6$: $PYR_{14}BOB:PYR_{14}TFSI$ ratio is 93%:5%:1 wt %:1 wt %. The number of charge and discharge life cycle of Negative A electrode in the resulting battery is 1345 and that of Negative B electrode is 299.

In Sample 14, the electrolyte comprises the $OE:PYR_{15}PF_6:PYR_{14}ODFB:PYR_{14}TFSI$ ratio is 93%:5%:1 wt %:1 wt %. The number of charge and discharge life cycle of Negative A electrode in the resulting battery is 1372 and that of Negative B electrode is 305.

In Sample 15, the electrolyte comprises the $OE:PYR_{15}PF_6:PYR_{14}BOB:PYR_{14}FSI$ ratio is 93%:5%:1 wt %:1 wt %. The number of charge and discharge life cycle of Negative A electrode in the resulting battery is 910 and that of Negative B electrode is 310.

In Sample 16, the electrolyte comprises OE, $PYR_{15}PF_6$, $PYR_{14}ODFB$ and $PYR_{14}FSI$ The $OE:PYR_{15}PF_6$: $PYR_{14}ODFB:PYR_{14}FSI$ ratio is 93%:5%:1 wt %:1 wt %. The number of charge and discharge life cycle of Negative A electrode in the resulting battery is 920 and that of Negative B electrode is 326.

In Sample 17, the electrolyte comprises OE. $PYR_{15}PF_6$, $PYR_{14}BOB$ and $PYR_{14}TFSI$. The $OE:PYR_{15}PF_6$: $PYR_{14}BOB:PYR_{14}TFSI$ ratio is 91%:5%:1 wt. %:3 wt %. The number of charge and discharge life cycle of Negative A electrode in the resulting battery is 1537 and that of Negative B electrode is 306.

In Sample 18, the electrolyte comprises OE, $PYR_{15}PF_6$, $PYR_{14}ODFB$ and $PYR_{14}TFSI$. The $OE:PYR_{15}PF_6$: $PYR_{14}ODFB:PYR_{14}TFSI$ ratio is 91%:5%:1 wt %:3 wt %. The number of charge and discharge life cycle of Negative A electrode in the resulting battery is 1587 and that of Negative B electrode is 328.

In Sample 19, the electrolyte comprises OE, $PYR_{15}PF_6$, $PYR_{14}BOB$ and $PYR_{14}FSI$. The $OE:PYR_{15}PF_6$: $PYR_{14}BOB:PYR_{14}FSI$ ratio is 91%:5%:1 wt %:3 wt %.

The number of charge and discharge life cycle of Negative A electrode in the resulting battery is 915 and that of Negative B electrode is 354.

In Sample 20, the electrolyte comprises OE, $PYR_{15}PF_6$, $PYR_{14}ODFB$ and $PYR_{14}FSI$. The $OE:PYR_{15}PF_6$: $PYR_{14}ODFB:PYR_{14}FSI$ ratio is 91%:5%:1 wt %:3 wt %. The number of charge and discharge life cycle of Negative A electrode in the resulting battery is 908 and that of Negative B electrode is 369.

In Sample 21, which is a control, the electrolyte comprises only 100 wt % OE. The number of charge and discharge life cycle of Negative A electrode in the resulting battery is 2163 and that of Negative B electrode is 513.

It is reasonable to conclude that the addition of a second stabilizer $PYR_{1R}$-bis(trifluoromethane)sulfonimide (TFSI) or $PYR_{1R}$-bis(fluorosulfonyl)imide (FSI) to the electrolyte of a battery with $OE+PYR_{1R}PF_6$ where R=2 to 10 and $PYR_{1R}$ boron-based first stabilizer will result in further improvement of the cycle life of that battery when compared to the battery with only a first stabilizer added to the electrolyte.

Battery Performance Test Performed on Batteries with Electrolytes that Contain First, Second and Third Stabilizers.

With refer to FIG. 10:

Battery performance test with the Neware Battery Performance Test System

The battery contains a positive electrode, a negative electrode, a separator and an electrolyte.

The positive electrode comprises 90 wt % $LiFePO_4$+5 wt % Super P+5 wt % PVDF.

The negative electrode comprises MCMB 92 wt %+Super P 5 wt %+3 wt % PVDF.

The separator comprises ceramic coated polypropylene separator with a thickness of 20 um.

The electrolyte comprises an organic electrolyte (OE) comprises 1M $LiPF_6$ with ethylene carbonate (EC)/dimethyl carbonate (DMC)/diethyl carbonate (DEC) (at 1:1:1 vol %)

and 3.5 wt % vinylene carbonate (VC), an ionic liquid (IL) comprises $PYR_{16}PF_6$, $PYR_{14}BOB$, $PYR_{14}TFSI$ at 10:1:4 wt % and a third stabilizer.

The battery is charged and discharged
Charge and discharge at 0.2 C-rate.

The Cut-off condition. The battery is considered to be invalid when the charge and discharge cycle capacity drops below 80% of the original capacity.

Different batteries with different amounts of third stabilizer are tested and the results are provided in FIG. 10

A self-extinguishing test is also performed. 1.2 g of the electrolyte is dropped on a 47 mm glass fiber membrane having a thickness of 0.5 mm. Ignition timing test. The results are listed in FIG. 10 as well.

The results show that the addition of the third stabilizer can most effectively improve the cycle life of the battery, while ensuring the safety of the battery. The third stabilizer can be any of the four additives as listed below:

1) Ethoxy(pentafluoro) cyclotriphosphazene (PFPN) is added in an amount of 0.5 to 10 wt. % of the electrolyte, and a more preferred embodiment is 0.5 to 2.9% of the electrolyte;
2) Ethylhexyl Diphenyl Phosphate (EHDP) is added in an amount of 0.5 to 5 wt. % of the electrolyte;
3) Hexaphenoxycyclotriphosphazene (HPCP) is added in an amount of 0.5 to 5% by weight of the electrolyte; and
4) 10-(2,5-dihydroxyphenyl)-9,10-dihydro-9-oxa-10-phosaaphenanthrene-10-oxide (DOPO-HQ) is added less than 1.5 wt. % of the electrolyte.

With reference to FIG. 10:

In Sample 1, the electrolyte comprises the OE, IL and PFPN. The OE:IL ratio is 85 wt %:15 wt. %. The OE+$PYR_{16}PF_6$, $PYR_{14}BOB$, $PYR_{14}TFSI$ (IL):PFPN ratio is 99.50 wt %:0.50 wt %. The number of charge and discharge life cycle of Negative A electrode in the resulting battery is 1674 and the self-extinguishing time is less than 6 second per gram.

In Sample 2, the electrolyte comprises the OE, IL and PFPN. The OE:IL ratio is 85 wt. %:15 wt. %. The OE+$PYR_{16}PF_6$, $PYR_{14}BOB$, $PYR_{14}TFSI$ (IL):PFPN ratio is 98 wt %:2 wt %. The number of charge and discharge life cycle of Negative A electrode in the resulting battery is 2291 and the self-extinguishing time is less than 6 second per gram.

In Sample 3, the electrolyte comprises the OE, IL and PFPN. The OE:IL ratio is 85 wt. % 15 wt. % The OE+$PYR_{16}PF_6$, $PYR_{14}BOB$, $PYR_{14}TFSI$ (IL):PFPN ratio is 97.50 wt %:2.50 wt % The number of charge and discharge life cycle of Negative A electrode in the resulting battery is 2308 and the self-extinguishing time is less than 6 second per gram.

In Sample 4, the electrolyte comprises the OE. IL and PFPN. The OE:IL ratio is 85 wt. %:15 wt. %. The OE+$PYR_{16}PF_6$, $PYR_{14}BOB$, $PYR_{14}TFSI$ (IL):PFPN ratio is 97.10 wt %:2.90 wt %. The number of charge and discharge life cycle of Negative A electrode in the resulting battery is 2315 and the self-extinguishing time is less than 6 second per gram.

In Sample 5, the electrolyte comprises the OE, IL and PFPN The OE:IL ratio is 85 wt. %:15 wt. %. The OE+$PYR_{16}PF_6$, $PYR_{14}BOB$, $PYR_{14}TFSI$ (IL):PFPN ratio is 97 wt %:3 wt %. The number of charge and discharge life cycle of Negative A electrode in the resulting battery is 2330 and the self-extinguishing time is less than 6 second per gram.

In Sample 6, the electrolyte comprises the OE, IL and PFPN. The OE:IL ratio is 85 wt. %:15 wt. % The OE+$PYR_{16}PF_6$, $PYR_{14}BOB$, $PYR_{14}TFSI$ (IL):PFPN ratio is (95 wt %:5 wt %). The number of charge and discharge life cycle of Negative A electrode in the resulting battery is 2392 and the self-extinguishing time is less than 6 second per gram.

In Sample 7, the electrolyte comprises the OE. IL and PFPN. The OE:IL ratio is 85 wt. %:15 wt. %. The OE+$PYR_{16}PF_6$, $PYR_{14}BOB$, $PYR_{14}TFSI$ (L):PFPN ratio is 90 wt %:10 wt % The number of charge and discharge life cycle of Negative A electrode in the resulting battery is 2432 and the self-extinguishing time is less than 6 second per gram.

In Sample 8, the electrolyte comprises the OE, IL and EHDP. The OE:IL ratio is 85 wt. %:15 wt. %. The OE+$PYR_{16}PF_6$, $PYR_{14}BOB$, $PYR_{14}TFSI$ (IL):EHDP ratio is 99.50 wt %:0.50 wt %. The number of charge and discharge life cycle of Negative A electrode in the resulting battery is 1637 and the self-extinguishing time is less than 6 second per gram.

In Sample 9, the electrolyte comprises the OE, IL and EHDP The OE:IL ratio is 85 wt. %/15 wt. % The OE+$PYR_{16}PF_6$, $PYR_{14}BOB$, $PYR_{14}TFSI$ (IL):EHDP ratio is 98 wt %:2 wt %. The number of charge and discharge life cycle of Negative A electrode in the resulting battery is 1943 and the self-extinguishing time is less than 6 second per gram.

In Sample 10, the electrolyte comprises the OE, IL and EHDP. The OE:IL ratio is 85 wt. %:15 wt. %. The OE+$PYR_{16}PF_6$, $PYR_{14}BOB$, $PYR_{14}TFSI$ (IL):EHDP ratio is (96.50 wt %:3.50 wt %). The number of charge and discharge life cycle of Negative A electrode in the resulting battery is 2098 and the self-extinguishing time is less than 6 second per gram.

In Sample 11, the electrolyte comprises the OE, IL and EHDP. The OE:IL ratio is 85 wt. %:15 wt. %. The OE+$PYR_{16}PF_6$, $PYR_{14}BOB$, $PYR_{14}TFSI$ (IL):EHDP ratio is 95.50 wt %:4.50 wt %. The number of charge and discharge life cycle of Negative A electrode in the resulting battery is 2158 and the self-extinguishing time is less than 6 second per gram.

In Sample 12, the electrolyte comprises the OE, IL and EHDP. The OE:IL ratio is 85 wt. %:15 wt. % The OE+$PYR_{16}PF_6$, $PYR_{14}BOB$, $PYR_{14}TFSI$ (IL):EHDP ratio is 95 wt %:5 wt %. The number of charge and discharge life cycle of Negative A electrode in the resulting battery is 2153 and the self-extinguishing time is less than 6 second per gram.

In Sample 13, the electrolyte comprises the OE, IL and HPCP. The OE:IL ratio is 85 wt. %:15 wt. %. The OE+$PYR_{16}PF_6$, $PYR_{14}BOB$, $PYR_{14}TFSI$ (IL):HPCP ratio is 99.50 wt %:0.50 wt %. The number of charge and discharge life cycle of Negative A electrode in the resulting battery is 1484 and the self-extinguishing time is less than 6 second per gram.

In Sample 14, the electrolyte comprises the OE, IL and HPCP. The OE:IL ratio is 85 wt. %:15 wt. %. The OE+$PYR_{16}PF_6$, $PYR_{14}BOB$, $PYR_{14}TFSI$ (IL):HPCP ratio is 98 wt %:2 wt %. The number of charge and discharge life cycle of Negative A electrode in the resulting battery is 1599 and the self-extinguishing time is less than 6 second per gram.

In Sample 15, the electrolyte comprises the OE, IL and HPCP. The OE:IL ratio is 85 wt. %:15 wt. % The OE+$PYR_{16}PF_6$, $PYR_{14}BOB$, $PYR_{14}TFSI$ (IL):HPCP ratio is 96.50 wt %:3.0 wt %. The number of charge and discharge life cycle of Negative A electrode in the resulting battery is 1932 and the self-extinguishing time is less than 6 second per gram.

In Sample 16, the electrolyte comprises the OE, IL and HPCP. The OE:IL ratio is 85 wt. %:15 wt. %. The OE+$PYR_{16}PF_6$, $PYR_{14}BOB$, $PYR_{14}TFSI$ (IL):HPCP ratio is 95.50 wt %:4.50 wt %. The number of charge and discharge life cycle of Negative A electrode in the resulting battery is 1908 and the self-extinguishing time is less than 6 second per gram.

In Sample 17, the electrolyte comprises the OE, IL and HPCP. The OE:IL ratio is 85 wt %:15 wt. %. The OE+$PYR_{16}PF_6$, $PYR_{14}BOB$, $PYR_{14}TFSI$ (IL):HPCP ratio is 95 wt %:5 wt % The number of charge and discharge life cycle of Negative A electrode in the resulting battery is 1956 and the self-extinguishing time is less than 6 second per gram.

In Sample 18, the electrolyte comprises the OE, IL and DOPO-HQ. The OE:IL ratio is 85 wt. %:15 wt. %. The OE+$PYR_{16}PF_6$, $PYR_{14}BOB$, $PYR_{14}TFSI$ (IL):DOPO-HQ ratio is 99.5 wt %:0.5 wt %. The number of charge and discharge life cycle of Negative A electrode in the resulting battery is 1957 and the self-extinguishing time is less than 6 second per gram.

In Sample 19, the electrolyte comprises the OE, IL and DOPO-HQ. The OE:IL ratio is 85 wt. %:15 wt. %. The OE+$PYR_{16}PF_6$, $PYR_{14}BOB$, $PYR_{14}TFSI$ (IL):DOPO-HQ ratio is 98.50 wt %:1.50 wt %. The number of charge and discharge life cycle of Negative A electrode in the resulting battery is 2084 and the self-extinguishing time is less than 6 second per gram.

In Sample 20, which is a control, the electrolyte comprises only OE. The number of charge and discharge life cycle of Negative A electrode in the resulting battery is 2163 and the self-extinguishing time is about 35 second per gram.

In Sample 21, which is a control, the electrolyte comprises OE and IL, OE:IL ratio is 85 wt %:15 wt %. The number of charge and discharge life cycle of Negative A electrode in the resulting battery is 1396 and the self-extinguishing time is less than 6 second per gram.

The addition of the third stabilizer renders the battery commercially useful as far as charging and discharging life cycles is concerned. However the side reactions as shown in FIG. 3 to 6 require attention. The addition of the flame retardant is necessary but brings about the unwanted side reaction. These side reactions are inhibited by the addition of the first and second stabilizers. The addition of the first and second stabilizers not only improves the charging and discharging life cycles but also to avoid the side reactions.

In FIG. 12, there is shown a cyclic voltammetry graph for a battery in which the electrolyte contains no $PYR_{1R}PF_6$ but organic electrolyte (OE) comprises 1M $LiPF_6$ with ethylene carbonate (EC)/dimethyl carbonate (DMC)/diethyl carbonate (DEC) (at 1:1:1 vol %) and 3.5 wt % vinylene carbonate (VC). There is no side reaction (redox reaction). This is confirmed by the experiment resulting in the findings in the table of FIG. 11. Upon the addition of $PYR_{1R}PF_6$, where R=any one of 2 to 10, side reactions are detected as shown detailed in FIG. 3.

One or more stabilizers are added with the intension to inhibit the side reaction as a result of the addition of $PYR_{1R}PF_6$, where R=any one of 2 to 10.

Referring to FIG. 11, the side reaction peak test is performed using a three-electrode test method measured by Autolab 302N electrochemical workstation. The working electrode is a Negative A electrode comprising MCMB 92 wt %+Super P 5 wt %+3 wt % PVDF.

The reference electrode comprises lithium metal.

The counter electrode comprises lithium metal.

The scan range is 0-2.5V and the scan rate is 1 mV/s.

Sample 1 in FIG. 11 is a control in which the electrolyte contains no $PYR_{1R}PF_6$ but organic electrolyte (OE) comprises 1M $LiPF_6$ with ethylene carbonate (EC)/dimethyl carbonate (DMC)/diethyl carbonate (DEC) (at 1:1:1 vol %) and 3.5 wt % vinylene carbonate (VC). There is no side reaction after testing as shown in the cyclic voltammetry graph of FIG. 12.

Sample 2 in FIG. 11 includes 85 wt % of OE, 10 wt % of $PYR_{16}PF_6$ and a first stabilizer 5 wt % of $PYR_{14}BF_4$ in the electrolyte. Side reaction is found after testing as shown in the cyclic voltammetry graph of FIG. 13.

Sample 3 in FIG. 11 includes 80 wt % of OE, 15 wt % of $PYR_{16}PF_6$ and a first stabilizer 5 wt % of $PYR_{14}ODFB$ in the electrolyte. No Side reaction is found after testing as shown in the cyclic voltammetry graph of FIG. 14.

Sample 4 in FIG. 11 includes 80 wt % of OE, 15 wt % of $PYR_{16}PF_6$ and a first stabilizer 5 wt % of $PYR_{14}BOB$ in the electrolyte. No Side reaction is found after testing as shown in the cyclic voltammetry graph of FIG. 15.

Sample 5 in FIG. 11 includes 85 wt % of OE, 10 wt % of $PYR_{16}PF_6$ and a second stabilizer 5 wt % of $PYR_{14}FSI$ in the electrolyte. Side reaction is found after testing as shown in the cyclic voltammetry graph of FIG. 16.

Sample 6 in FIG. 11 includes 85 wt % of OE, 10 wt % of $PYR_{16}PF_6$ and a second stabilizer 5 wt % of $PYR_{14}TFSI$ in the electrolyte. Side reaction is found after testing as shown in the cyclic voltammetry graph of FIG. 17.

Sample 7 in FIG. 11 includes 80 wt % of OE, 14 wt % of $PYR_{16}PF_6$, 1 wt % $PYR_{14}BOB$ as a first stabilizer and a second stabilizer 5 wt % of $PYR_{14}TFSI$ in the electrolyte. No side reaction is found after testing as shown in the cyclic voltammetry graph of FIG. 18.

Sample 8 in FIG. 11 includes 80 wt % of OE, 9 wt % of $PYR_{16}PF_6$, 1 wt % $PYR_{14}BOB$ as a first stabilizer and a second stabilizer 10 wt % of $PYR_{14}TFSI$ in the electrolyte. No side reaction is found after testing as shown in the cyclic voltammetry graph of FIG. 19.

As noted in Sample 2, the first stabilizer-$PYR_{1R}$boron-based ionic liquid and the anion of $BF_4$ do not contribute to the inhibition of the side reaction peak. As shown in Samples 5 and 6, when there is only a second stabilizer being used with $PYR_{16}PF_6$ i.e. without a first stabilizer, no inhibition of the side reaction peak is observed. When the first stabilizer is used without a second stabilizer, it seems to be slightly more effective than the use of second stabilizer without a first stabilizer as can be seen from the results of Samples 3 and 4 in comparison with Samples 5 and 6.

Example 1

Battery Performance Tests Performed on Batteries of the Invention with Electrolytes that Contain a First, a Second and a Third Stabilizer The organic solvent 1M $LiPF_6$ with ethylene carbonate (EC)/dimethyl carbonate (DMC)/diethyl carbonate (DEC) (at 1:1:1 vol %) and 3.5 wt % vinylene carbonate (VC) is mixed with $PYR_{16}PF_6$ as the flame retardant, $PYR_{14}BOB$ as the first stabilizer, $PYR_{14}TFSI$ as the second stabilizer to form a main solvent of the electrolyte. The main solvent is tested with different amount of third stabilizer selected from a group consisting of PFPN, EHDP, HPCP and DOPO-HQ.

The resulting battery is tested with the Neware Battery Performance Test System.

Battery performance test with reference to FIG. 20:

The battery contains a positive electrode, a negative electrode, a separator and an electrolyte.

The positive electrode comprises a composition of 90 wt % $LiFePO_4$+5 wt % Super P+5 wt % PVDF.

The negative A electrode comprises a composition of MCMB 92 wt %+Super P 5 wt %+3 wt % PVDF.

The separator comprises of ceramic coated polypropylene separator with a thickness of 20 um.

The electrolyte comprises the OE, $PYR_{16}PF_6$ as the flame retardant, $PYR_{14}BOB$ as the first stabilizer. $PYR_{14}TFSI$ as the second stabilizer and a third stabilizer as detailed in FIG. 20.

The resulting battery is charged and discharged at 0.2 C-rate. The cut-off condition is when the battery is judged to be invalid i.e. when the charge and discharge cycle capacity drops below 80% of the original capacity.

Self-extinguishing test is performed by dropping 1.2 g of the electrolyte on a 47 mm glass fiber membrane having a thickness of 0.5 mm. The self-extinguishing time is recorded.

With reference to FIG. 20

In Sample 1, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}BOB$, $PYR_{14}TFSI$ at 1:0.5:1 wt % and PFPN as a third stabilizer at 2.0 wt %. The number of charge and discharge life cycle of electrode A in the resulting battery is 2013 and the self-extinguishing time is less than 12 second per gram.

In Sample 2, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}BOB$, $PYR_{14}TFSI$ at 1:0.5:1 wt % and PFPN a third stabilizer at 2.5 wt %. The number of charge and discharge life cycle of electrode A in the resulting battery is 2089 and the self-extinguishing time is less than 8 second per gram.

In Sample 3, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}BOB$, $PYR_{14}TFSI$ at 1:0.5:1 wt % and PFPN_a third stabilizer at 2.9 wt %. The number of charge and discharge life cycle of electrode A in the resulting battery is 2149 and the self-extinguishing time is less than 8 second per gram.

In Sample 4, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}BOB$, $PYR_{14}TFSI$ at 1:0.5:1 wt % and PFPN_a third stabilizer at 3.0 wt %. The number of charge and discharge life cycle of electrode A in the resulting battery is 2315 and the self-extinguishing time is less than 6 second per gram.

In Sample 5, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}BOB$, $PYR_{14}TFSI$ at 1:0.5:1 wt % and PFPN_a third stabilizer at 4 wt %. The number of charge and discharge life cycle of electrode A in the resulting battery is 2317 and the self-extinguishing time is less than 6 second per gram.

In Sample 6, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}BOB$, $PYR_{14}TFSI$ at 1:0.5:1 wt % and PFPN_a third stabilizer at 5 wt %. The number of charge and discharge life cycle of electrode A in the resulting battery is 2340 and the self-extinguishing time is less than 6 second per gram.

In Sample 7, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}BOB$, $PYR_{14}TFSI$ at 1:0.5:1 wt % and PFPN_a third stabilizer at 10 wt %. The number of charge and discharge life cycle of electrode A in the resulting battery is 2452 and the self-extinguishing time is less than 6 second per gram.

In Sample 8, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}BOB$, $PYR_{14}TFSI$ at 1:0.5:1 wt % and EHDP as a third stabilizer at 4.50 wt %. The number of charge and discharge life cycle of electrode A in the resulting battery is 2173 and the self-extinguishing time is less than 7 second per gram.

In Sample 9, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}BOB$, $PYR_{14}TFSI$ at 1:0.5:1 wt % and EHDP as a third stabilizer at 5 wt %. The number of charge and discharge life cycle of electrode A in the resulting battery is 2188 and the self-extinguishing time is less than 6 second per gram.

In Sample 10, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}BOB$, $PYR_{14}TFSI$ at 1:0.5:1 wt % and HPCP as a third stabilizer at 4.50 wt %. The number of charge and discharge life cycle of electrode A in the resulting battery is 2098 and the self-extinguishing time is less than 6 second per gram.

In Sample 11, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}BOB$, $PYR_{14}TFSI$ at 1:0.5:1 wt % and HPCP as a third stabilizer at 5 wt %. The number of charge and discharge life cycle of electrode A in the resulting battery is 2134 and the self-extinguishing time is less than 6 second per gram.

In Sample 12, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}BOB$, $PYR_{14}TFSI$ at 1:0.5:1 wt % and DOPO-HQ as a third stabilizer at 1.50 wt %. The number of charge and discharge life cycle of electrode A in the resulting battery is 2102 and the self-extinguishing time is less than 10 second per gram.

In Sample 13, it is a control, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC). The number of charge and discharge life cycle of electrode A electrode in the resulting battery is 2163 and the self-extinguishing time is 35 second per gram.

In Sample 14, it is a control, the electrolyte comprises organic electrolyte (OE) 1M $LiPF_6$ with ethylene carbonate (EC)/dimethyl carbonate (DMC)/diethyl carbonate (DEC)

(at 1:1:1 vol %) and 3.5 wt % vinylene carbonate (VC) and $PYR_{16}PF_6$, $PYR_{14}BOB$, $PYR_{14}TFSI$ at 1:0.5:1 wt %. The number of charge and discharge life cycle of electrode A in the resulting battery is 1873 and the self-extinguishing time is less than 25 second per gram.

Example 2

Battery Performance Tests Performed on Batteries of the Invention with Electrolytes that Contain a First, a Second and a Third Stabilizer The organic electrolyte (OE) comprises 1M $LiPF_6$ with ethylene carbonate (EC)/dimethyl carbonate (DMC)/diethyl carbonate (DEC) (at 1:1:1 vol %) and 3.5 wt % vinylene carbonate (VC) is mixed with $PYR_{16}PF_6$ as the flame retardant, $PYR_{14}ODFB$ as the first stabilizer, $PYR_{13}TFSI$ as the second stabilizer to form a main solvent of the electrolyte. The main solvent is tested with different amount of third stabilizer selected from a group consisting of PFPN, EHDP, HPCP and DOPO-HQ.

The resulting battery is tested with the Neware Battery Performance Test System.

Battery performance test with reference to FIG. 21:

The battery contains a positive electrode, a negative electrode, a separator and an electrolyte.

The positive electrode comprises a composition of 90 wt % $LiFePO_4$+5 wt % Super P+5 wt % PVDF The negative A electrode comprises a composition of MCMB 92 wt %-+Super P 5 wt %3 wt % PVDF The separator comprises of ceramic coated polypropylene separator with a thickness of 20 um.

The electrolyte comprises the (OE), $PYR_{16}PF_6$ as the flame retardant, $PYR_{14}ODFB$ as the first stabilizer, $PYR_{13}TFSI$ as the second stabilizer and a third stabilizer as detailed in FIG. 21.

The resulting battery is charged and discharged at 0.2 C-rate. The cut-off condition is when the battery is judged to be invalid i.e. when the charge and discharge cycle capacity drops below 80% of the original capacity.

Self-extinguishing test is performed by dropping 1.2 g of the electrolyte on a 47 mm glass fiber membrane having a thickness of 0.5 mm. The self-extinguishing time is recorded.

With reference to FIG. 21

In Sample 1, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}ODFB$, $PYR_{13}TFSI$ at 1:0.5:1 wt % and PFPN as a third stabilizer at 2.5 wt %. The number of charge and discharge life cycle of electrode A in the resulting battery is 2078 and the self-extinguishing time is less than 8 second per gram.

In Sample 2, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}ODFB$, $PYR_{13}TFSI$ at 1:0.5:1 wt % and PFPN a third stabilizer at 2.9 wt %. The number of charge and discharge life cycle of electrode A in the resulting battery is 2102 and the self-extinguishing time is less than 8 second per gram.

In Sample 3, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}ODFB$, $PYR_{13}TFSI$ at 1:0.5:1 wt % and PFPN_a third stabilizer at 3.0 wt %. The number of charge and discharge life cycle of electrode A electrode in the resulting battery is 2311 and the self-extinguishing time is less than 6 second per gram.

In Sample 4, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}ODFB$, $PYR_{13}TFSI$ at 1:0.5:1 wt % and PFPN_a third stabilizer at 4 wt %. The number of charge and discharge life cycle of electrode A in the resulting battery is 2315 and the self-extinguishing time is less than 6 second per gram.

In Sample 5, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}ODFB$, $PYR_{13}TFSI$ at 1:0.5:1 wt % and PFPN_a third stabilizer at 5 wt %. The number of charge and discharge life cycle of electrode A in the resulting battery is 2338 and the self-extinguishing time is less than 6 second per gram.

In Sample 6, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}ODFB$, $PYR_{13}TFSI$ at 1:0.5:1 wt % and PFPN_a third stabilizer at 10 wt %. The number of charge and discharge life cycle of electrode A in the resulting battery is 2433 and the self-extinguishing time is less than 6 second per gram.

In Sample 7, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}ODFB$, $PYR_{13}TFSI$ at 1:0.5:1 wt % and EHDP as a third stabilizer at 4.50 wt %. The number of charge and discharge life cycle of electrode A in the resulting battery is 2149 and the self-extinguishing time is less than 7 second per gram.

In Sample 8, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}ODFB$, $PYR_{13}TFSI$ at 1:0.5:1 wt % and EHDP as a third stabilizer at 5 wt %. The number of charge and discharge life cycle of electrode A electrode in the resulting battery is 2176 and the self-extinguishing time is less than 6 second per gram.

In Sample 9, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}ODFB$, $PYR_{13}TFSI$ at 1:0.5:1 wt % and HPCP as a third stabilizer at 4.50 wt %. The number of charge and discharge life cycle of electrode A in the resulting battery is 2055 and the self-extinguishing time is less than 6 second per gram.

In Sample 10, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}ODFB$, $PYR_{13}TFSI$ at 1:0.5:1 wt % and HPCP as a third stabilizer at 5 wt %. The number of charge and discharge life cycle of electrode A in the resulting battery is 2122 and the self-extinguishing time is less than 6 second per gram.

In Sample 11, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}ODFB$, $PYR_{13}TFSI$ at 1:0.5:1 wt % and DOPO-HQ as a third stabilizer at 1.50 wt %. The number of charge and discharge life cycle of electrode A in the resulting battery is 2095 and the self-extinguishing time is less than 10 second per gram.

In Sample 13, it is a control, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC). The number of charge and discharge life cycle of electrode A in the resulting battery is 2163 and the self-extinguishing time is 35 second per gram.

In Sample 14, it is a control, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC) and $PYR_{16}PF_6$, $PYR_{14}ODFB$, $PYR_{13}TFSI$ at 1:0.5:1 wt %. The number of charge and discharge life cycle of electrode A in the resulting battery is 1824 and the self-extinguishing time is less than 25 second per gram.

Example 3

Battery Performance Tests Performed on Batteries of the Invention with Electrolytes that Contain a First, a Second and a Third Stabilizer The organic solvent (OE) comprises 1M $LiPF_6$ with ethylene carbonate (EC)/dimethyl carbonate (DMC)/diethyl carbonate (DEC) (at 1:1:1 vol %) and 3.5 wt % vinylene carbonate (VC) is mixed with $PYR_{16}PF_6$ as the flame retardant, $PYR_{14}ODFB$ as the first stabilizer. $PYR_{13}TFSI$ as the second stabilizer to form a main solvent of the electrolyte. The main solvent is tested with different amount of third stabilizer selected from a group consisting of PFPN, EHDP, HPCP and DOPO-HQ.

The resulting battery is tested with the Neware Battery Performance Test System.

Battery performance test with reference to FIG. 22.

The battery contains a positive electrode, a negative electrode, a separator and an electrolyte.

The positive electrode comprises a composition of 90 wt % $LiFePO_4$+5 wt % Super P+5 wt % PVDF.

The negative A electrode comprises a composition of MCMB 92 wt %+Super P 5 wt %+3 wt % PVDF The separator comprises of ceramic coated polypropylene separator with a thickness of 20 um.

The electrolyte comprises the OE, $PYR_{16}PF_6$ as the flame retardant, $PYR_{14}ODFB$ as the first stabilizer, $PYR_{13}TFSI$ as the second stabilizer and a third stabilizer as detailed in FIG. 22.

The resulting battery is charged and discharged at 0.2 C-rate. The cut-off condition is when the battery is judged to be invalid i.e. when the charge and discharge cycle capacity drops below 80% of the original capacity.

Self-extinguishing test is performed by dropping 1.2 g of the electrolyte on a 47 mm glass fiber membrane having a thickness of 0.5 mm. The self-extinguishing time is recorded.

With reference to FIG. 22

In Sample 1, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}ODFB$, $PYR_{13}TFSI$ at 10:1:4 wt % and PFPN as a third stabilizer at 2.50 wt %. The number of charge and discharge life cycle of electrode A in the resulting battery is 2251 and the self-extinguishing time is less than 6 second per gram.

In Sample 2, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}ODFB$, $PYR_{13}TFSI$ at 10:1:4 wt % and PFPN a third stabilizer at 2.90 wt %. The number of charge and discharge life cycle of electrode A in the resulting battery is 2294 and the self-extinguishing time is less than 6 second per gram.

In Sample 3, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}ODFB$, $PYR_{13}TFSI$ at 10:1:4 wt % and PFPN_a third stabilizer at 3 wt %. The number of charge and discharge life cycle of electrode A in the resulting battery is 2315 and the self-extinguishing time is less than 6 second per gram.

In Sample 4, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}ODFB$, $PYR_{13}TFSI$ at 10:1:4 wt % and PFPN_a third stabilizer at 5 wt %. The number of charge and discharge life cycle of electrode A in the resulting battery is 2337 and the self-extinguishing time is less than 6 second per gram.

In Sample 5, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}ODFB$, $PYR_{13}TFSI$ at 10:1:4 wt % and PFPN_a third stabilizer at 10 wt %. The number of charge and discharge life cycle of electrode A in the resulting battery is 2356 and the self-extinguishing time is less than 6 second per gram.

In Sample 6, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}ODFB$, $PYR_{13}TFSI$ at 10:1:4 wt % and EHDP as a third stabilizer at 3.50 wt %. The number of charge and discharge life cycle of electrode A in the resulting battery is 2043 and the self-extinguishing time is less than 6 second per gram.

In Sample 7, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}ODFB$, $PYR_{13}TFSI$ at 10:1:4 wt % and EHDP as a third stabilizer at 4.50 wt %. The number of charge and discharge life cycle of electrode A in the resulting battery is 2098 and the self-extinguishing time is less than 6 second per gram.

In Sample 8, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}ODFB$, $PYR_{13}TFSI$ at 10:1:4 wt % and EHDP as a third stabilizer at 5 wt %. The number of charge and discharge life cycle of electrode A electrode in the resulting battery is 2156 and the self-extinguishing time is less than 6 second per gram.

In Sample 9, the electrolyte comprises organic electrolyte (OE) 1M $LiPF_6$ with ethylene carbonate (EC)/dimethyl carbonate (DMC)/diethyl carbonate (DEC) (at 1:1:1 vol %)

and 3.5 wt % vinylene carbonate (VC), $PYR_{16}PF_6$, $PYR_{14}ODFB$, $PYR_{13}TFSI$ at 10:1:4 wt % and HPCP as a third stabilizer at 3.50 wt %. The number of charge and discharge life cycle of electrode A in the resulting battery is 1894 and the self-extinguishing time is less than 6 second per gram.

In Sample 10, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}ODFB$, $PYR_{13}TFSI$ at 10:1:4 wt % and HPCP as a third stabilizer at 4.50 wt %. The number of charge and discharge life cycle of electrode A in the resulting battery is 1902 and the self-extinguishing time is less than 6 second per gram.

In Sample 11, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}ODFB$, $PYR_{13}TFSI$ at 10:1:4 wt % and HPCP as a third stabilizer at 5 wt %. The number of charge and discharge life cycle of electrode A in the resulting battery is 1941 and the self-extinguishing time is less than 6 second per gram.

In Sample 12, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC), $PYR_{16}PF_6$, $PYR_{14}ODFB$, $PYR_{13}TFSI$ at 10:1:4 wt % and DOPO-HQ as a third stabilizer at 1.50 wt %. The number of charge and discharge life cycle of electrode A in the resulting battery is 2096 and the self-extinguishing time is less than 6 second per gram.

In Sample 13, it is a control, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC). The number of charge and discharge life cycle of electrode A in the resulting battery is 2163 and the self-extinguishing time is 35 second per gram.

In Sample 14, it is a control, the electrolyte comprises organic electrolyte (OE) 1M $LiPF_6$ with ethylene carbonate (EC)/dimethyl carbonate (DMC)/diethyl carbonate (DEC) (at 1:1:1 vol %) and 3.5 wt % vinylene carbonate (VC) and $PYR_{16}PF_6$, $PYR_{14}ODFB$, $PYR_{13}TFSI$ at 10:1:4 wt %. The number of charge and discharge life cycle of electrode A in the resulting battery is 1361 and the self-extinguishing time is less than 6 second per gram.

Examples 1 and 2 are the most cost effective embodiments of the invention while Example 3 is the embodiment that has the best performance.

The invention has been given by way of example only, and various other modifications of and/or alterations to the described embodiment may be made by persons skilled in the art without departing from the scope of the invention as specified in the appended claims.

The invention claimed is:

1. An electrolyte for a lithium-ion battery comprising:
a lithium salt, and
a non-aqueous organic solvent which includes a carbonate-based solvent, a flame retardant, a film former, and a stabilizing medium,
wherein
the flame retardant comprises an N-methyl-N-alkylpyrrolidinium hexafluorophosphate salt in an amount of 1 to 15 wt. % of the electrolyte,
the stabilizing medium comprises a first stabilizer, a second stabilizer, and a third stabilizer, and
the third stabilizer is selected from the group consisting of hexaphenoxycyclotriphosphazene (HPCP) in an amount between 0.5 to 5 wt. % of the electrolyte and 10-(2,5-dihydroxyphenyl)-9,10-dihydro-9-oxa-10-phosphaphenanthrene-10-oxide (DOPO-HO) in an amount less than or equal to 1.5 wt. % of the electrolyte.

2. The electrolyte as claimed in claim 1, wherein the N-methyl-N-alkylpyrrolidinium hexafluorophosphate salt is of the formula $PYR_{1R}PF_6$, wherein the subscript R indicates the number of carbon atoms in the N-alkyl group, in which the subscript R is selected from any one of 2 to 10.

3. The electrolyte as claimed in claim 2, wherein the $PYR_{1R}PF_6$ has a melting point greater than 200° C.

4. The electrolyte as claimed in claim 3, wherein R is 2, 5, or 6.

5. The electrolyte as claimed in claim 1, wherein the first stabilizer comprises an ionic liquid with a $PYR_{1R}^+$ cation and a boron-based anion other than $BF_4^-$, wherein $PYR_{1R}^+$ is an N-methyl-N-alkylpyrrolidinium cation, and subscript R indicates the number of carbon atoms in the N-alkyl group.

6. The electrolyte as claimed in claim 5, wherein subscript R is 2, 3, 4, 5, or 6.

7. The electrolyte as claimed in claim 6, wherein the boron-based anion is selected from the group consisting of bis(oxalateborate) ($BOB^-$), difluoro(oxalate)borate ($ODFB^-$), and bis(mandelato)borate (BMW).

8. The electrolyte as claimed in claim 5, wherein the first stabilizer is present in an amount between 0 to 5 wt. % of the electrolyte.

9. The electrolyte as claimed in claim 1, wherein the second stabilizer comprises an ionic liquid with a $PYR_{1R}^+$ cation, wherein subscript R indicates the number of carbon atoms in the N-alkyl group of the N-methyl-N-alkylpyrrolidinium cation.

10. The electrolyte as claimed in claim 9, wherein R is 3 or 4.

11. The electrolyte as claimed in claim 10, wherein the second stabilizer comprises an ionic liquid with an anion selected from the group consisting of $TFSI^-$ and $FR^-$.

12. The electrolyte as claimed in claim 9, wherein the second stabilizer is present in an amount between 0 to 10 wt. % of the electrolyte.

13. The electrolyte as claimed in claim 1, wherein the non-aqueous organic solvent comprises carbonate-based organic solvents.

14. The electrolyte as claimed in claim 13, wherein the carbonate-based organic solvents are selected from the group consisting of ethylene carbonate (EC), ethyl methyl carbonate (EMC), diethyl carbonate (DEC), Propylene carbonate (PC), dimethyl carbonate (DMC), and mixtures thereof.

15. The electrolyte as claimed in claim 1, wherein the film former is selected from the group consisting of vinylene carbonate (VC) and fluoroethylene carbonate (FEC).

16. The electrolyte as claimed in claim 1, wherein the lithium salt comprises lithium hexafluorophosphate ($LiPF_6$).

17. An electrolyte for a lithium-ion battery comprising:
a lithium salt comprising $LiPF_6$, a non-aqueous organic solvent which includes a carbonate-based organic solvent, a flame retardant, a film former, and a stabilizing medium,
wherein
the carbonate-based organic solvent is selected from the group consisting of ethylene carbonate (EC), ethyl methyl carbonate (EMC), diethyl carbonate (DEC), Propylene carbonate (PC), dimethyl carbonate (DMC), and mixtures thereof;

the flame retardant comprises $PYR_{16}PF_6$;

the film former is selected from the group consisting of vinylene carbonate (VC) and fluoroethylene carbonate (FEC);

the stabilizing medium comprises a first stabilizer, a second stabilizer, and a third stabilizer;

the first stabilizer is selected from the group consisting of bis(oxalateborate) ($BOB^-$), and difluoro(oxalate)borate ($ODFB^-$), and the second stabilizer is selected from the group consisting of
(i) $PYR_{14}TFSI$ at a ratio of $PYR_{16}PF_6$:first stabilizer: $PYR_{14}TFSI$ being 1:0.5:1 wt. % of the electrolyte,
(ii) $PYR_{13}TFSI$ at a ratio of $PYR_{16}PF_6$:first stabilizer: $PYR_{13}TFSI$ being 1:0.5:1 wt. % of the electrolyte, and
(iii) $PYR_{13}TFSI$ at a ratio of $PYR_{16}PF_6$:first stabilizer: $PYR_{13}TFSI$ being 10:1:4 wt. % of the electrolyte.

18. The electrolyte as claimed in claim 17, wherein
the third stabilizer is selected from the group consisting of Ethoxy(pentafluoro) cyclotriphosphazene (PFPN), Ethylhexyl Diphenyl Phosphate (EHDP), Hexaphenoxycyclotriphosphazene (HPCP), and 10 (2,5-dihydroxyphenyl)-9,10-dihydro-9-oxa-10-phosphaphenanthrene-10-oxide (DOPO-HQ).

19. The electrolyte as claimed in claimed in claim 18, wherein
the first stabilizer is $PYR_{14}BOB$; and
the second stabilizer is $PYR_{14}TFSI$ at a ratio of 1:0.5:1 wt. % of the electrolyte.

20. The electrolyte as claimed in claimed in claim 18, wherein
the first stabilizer is $PYR_{14}ODFB$; and
the second stabilizer is $PYR_{14}TFSI$ at a ratio of 1:0.5:1 wt. % of the electrolyte.

21. The electrolyte as claimed in claimed in claim 18, wherein
the first stabilizer is $PYR_{14}ODFB$; and
the second stabilizer is $PYR_{13}TFSI$ at a ratio of 10:1:4 wt. % of the electrolyte.

22. The electrolyte as claimed in claim 18, wherein the PFPN is present in an amount between 0.5 to 10 wt. % of the electrolyte.

23. The electrolyte as claimed in claim 22, wherein the PFPN is present in an amount between 0.5 to 2.9 wt. % of the electrolyte.

24. The electrolyte as claimed in claim 18, wherein the EHDP is present in an amount between 0.5 to 5 wt. % of the electrolyte.

25. The electrolyte as claimed in claim 18, wherein the HPCP is present in an amount between 0.5 to 5 wt. % of the electrolyte.

26. The electrolyte as claimed in claim 18, wherein the DOPO-HQ is present in an amount less than or equal to 1.5 wt. % of the electrolyte.

27. The electrolyte as claimed in claim 17, wherein
the carbonate-based organic solvent comprises EC, DMC and DEC at in a ratio of 1:1:1 vol. %, and
the film former comprises 3.5 wt. % of the VC.

* * * * *

UNITED STATES PATENT AND TRADEMARK OFFICE
CERTIFICATE OF CORRECTION

| | | |
|---|---|---|
| PATENT NO. | : 10,763,547 B1 | Page 1 of 1 |
| APPLICATION NO. | : 16/733608 | |
| DATED | : September 1, 2020 | |
| INVENTOR(S) | : Wang | |

It is certified that error appears in the above-identified patent and that said Letters Patent is hereby corrected as shown below:

In the Claims

Claim 1 at Column 32, Line 7:
"(DOPO-HO)" should be replaced with "(DOPO- HQ)"

Claim 7 at Column 32, Line 29:
"(BMW)" should be replaced with "(BMB$^-$)"

Claim 11 at Column 32, Line 42:
"FR$^-$" should be replaced with "FSI$^-$"

Signed and Sealed this
Second Day of February, 2021

Drew Hirshfeld
*Performing the Functions and Duties of the*
*Under Secretary of Commerce for Intellectual Property and*
*Director of the United States Patent and Trademark Office*